United States Patent
Johnson et al.

(10) Patent No.: US 9,587,211 B2
(45) Date of Patent: Mar. 7, 2017

(54) PHOTO-BIOREACTOR SYSTEM AND METHOD

(75) Inventors: Wayne L. Johnson, Phoenix, AZ (US); Steven T. Fink, Mesa, AZ (US)

(73) Assignee: Arizona Technology Innovation Group, Inc., Phoenix, AZ (US)

( * ) Notice: Subject to any disclaimer, the term of this patent is extended or adjusted under 35 U.S.C. 154(b) by 675 days.

(21) Appl. No.: 13/452,442

(22) Filed: Apr. 20, 2012

(65) Prior Publication Data

US 2012/0270304 A1    Oct. 25, 2012

Related U.S. Application Data

(60) Provisional application No. 61/477,487, filed on Apr. 20, 2011.

(51) Int. Cl.
| | | |
|---|---|---|
| *C12M 1/00* | (2006.01) | |
| *C12M 3/00* | (2006.01) | |
| *C12M 1/34* | (2006.01) | |

(52) U.S. Cl.
CPC ............ *C12M 21/02* (2013.01); *C12M 27/20* (2013.01); *C12M 31/10* (2013.01); *C12M 41/00* (2013.01); *C12M 41/10* (2013.01); *C12M 41/26* (2013.01); *C12M 41/32* (2013.01); *C12M 41/36* (2013.01); *C12M 43/02* (2013.01)

(58) Field of Classification Search
CPC ..................................................... C12M 21/00
USPC ........................................ 435/292.1; 47/1.4
See application file for complete search history.

(56) References Cited

U.S. PATENT DOCUMENTS

| | | | | |
|---|---|---|---|---|
| 5,104,803 | A * | 4/1992 | Delente ...................... | 435/292.1 |
| 5,162,051 | A * | 11/1992 | Hoeksema ....................... | 47/1.4 |
| 6,083,740 | A * | 7/2000 | Kodo ..................... | B01D 53/84 |
| | | | | 435/257.1 |
| 2008/0044887 | A1* | 2/2008 | Maltezos et al. .......... | 435/257.1 |
| 2008/0086939 | A1* | 4/2008 | Dunlop et al. .................... | 47/1.4 |
| 2008/0274494 | A1* | 11/2008 | Kertz ....................... | A01G 7/02 |
| | | | | 435/29 |
| 2009/0047722 | A1* | 2/2009 | Wilkerson .............. | C12M 21/02 |
| | | | | 435/173.7 |
| 2010/0193011 | A1* | 8/2010 | Mapel ..................... | C03C 3/102 |
| | | | | 136/246 |
| 2010/0255458 | A1* | 10/2010 | Kinkaid ............................ | 435/3 |
| 2010/0330652 | A1* | 12/2010 | Mohr ..................... | C12M 21/02 |
| | | | | 435/243 |

(Continued)

OTHER PUBLICATIONS

Posten, C. (2009) Eng. Life Sci.9, No. 3, 165-177.*

(Continued)

*Primary Examiner* — Michael Hobbs
(74) *Attorney, Agent, or Firm* — Jennings Strouss & Salmon PLC; Michael K. Kelly

(57) ABSTRACT

A photo-bioreactor system for growing and harvesting photosynthetic organisms includes an interior space partitioned into a plurality of independently controlled reactor cells, each stepped downward along a slope from a first elevation to a second elevation, and a light source coupled to each reactor cell and configured to illuminate the photosynthetic organisms with first and second light-emitting surfaces. The system includes a fluid circulation system coupled to the reactor container and configured to force a continuous flow of fluid through the cell passages.

20 Claims, 17 Drawing Sheets

(56) References Cited

U.S. PATENT DOCUMENTS

2011/0078949 A1* 4/2011 Schuster ............... C12M 21/02
  47/1.4
2011/0117632 A1* 5/2011 Woerlee et al. ........... 435/257.1

OTHER PUBLICATIONS

Borowitzka, M. (1996) J. Marine Biotechnol. 4: 185-191.*
Merchuk et al. (2007) Chem. Biochem Eng. Q 21 (4): 345-355.*
Pulz et al. (1998) Advances in Biochemical Engineering/Biotechnology, vol. 59, 123-152.*
Chen et al. (2011) Bioresource Technology 102, 71-81.*
Akkerman, et al. (2002) International Journal of Hydrogen Energy 27, 1195-1208.*
Website document entitled "Light-emitting diode" (available at http://en.wikipedia.org/wiki/Light-emitting_diode). Archived Jun. 2004. Downloaded from websited Nov. 24, 2014.*
Lee et al. (1994) Biotechnology and Bioengineering, vol. 44, pp. 1161-1167.*
Becker, E.W. Microalgae: Biotechnology and microbiology. 1994. Chapter 10: Large Scale Cultivation. pp. 87-92.*

* cited by examiner

PHOTO-BIOREACTOR SYSTEM AND METHOD

CROSS-REFERENCE TO RELATED APPLICATIONS

Pursuant to 37 CFR §1.78(a)(4), this application claims the benefit of and priority to U.S. Provisional Application No. 61/477,487, filed on Apr. 20, 2011, the entire content of which is herein incorporated by reference.

BACKGROUND OF THE INVENTION

Field of Invention

The invention relates to systems and methods for cultivating photoautotrophic microorganisms.

Description of Related Art

A photoautotrophic microorganism is an organism that is capable of generating its own sustenance from inorganic substances using light as an energy source. As an example, photosynthetic microscopic algae, hereinafter referred to as algae, is a photoautotroph. Algae are unicellular organisms which produce oxygen by photosynthesis, and may include flagellates, diatoms, and blue-green algae. More than 100,000 species of algae are known.

As mentioned above, algae use a photosynthetic process similar to that of higher-developed plants, with certain advantages not found in traditional crops, such as rapeseed, wheat, or corn. Algae have a high growth rate, and it is possible to complete an entire harvest in hours. Further, algae are tolerant to varying environmental conditions, for example, algae may be grown in saline waters that are unsuitable for agriculture. Due to this tolerance to environment and climate, algae are responsible for about one-third of the net photosynthetic activity worldwide.

As a result, during the past decade, much focus has been aimed at the production of algae for commercial purposes. This focus is evidenced by the manifestation of many new industries and uses of algal production, including but not limited to the following: (i) use of algae as a source of fatty acids, proteins and other bio-chemicals in the production of nutraceuticals, health food, food additives, vitamins, pharmaceuticals, and natural dyes; (ii) use of algae as an animal feed supplement with nutritional value equivalent to that of soybean meal; (iii) use of algae as a biological control of agricultural pests; (iv, use of algae as soil conditioners and bio-fertilizers in agriculture; (v) use of algae for the production of oxygen and removal of nitrogen, phosphorus, and toxic substances in sewage treatment; (vi) use of algae in the bio-degradation of plastics; (vii) use of algae as a renewable biomass source for the production of a diesel fuel substitute (biodiesel) and other biofuels such as ethanol, methane gas, and hydrogen; and (viii) use of algae to scrub $CO_2$, $NO_x$, $VO_x$ from effluent released during the production of fossil fuel. With so many uses, it would be desirable to mass produce algae in a low-cost, high-yield manner.

One commercial purpose of significant import includes algae cultivation as a renewable biomass source for sustainable biodiesel production. Presently, the renewable biomass source is provided by edible oils, such as soybean oil, palm oil, and rapeseed oil. It is of interest to develop additional types of renewable biomass sources, such as lipids from algae.

As briefly noted above, one factor making algae interesting as a renewable biomass source is that algae may be grown under conditions or in places not suitable to other sources. Accordingly, algae may be grown and used in ways that do not significantly compete with food sources or agriculturally productive land.

An additional factor making algae of interest is the availability of material to convert to biodiesel or other fuel. Some algae have a lipid content as much as 50% to 70% of their dry weight. By way of comparison, the lipid content in dry soybeans is approximately 20%. Algal lipids have a similar composition to vegetable oil and are readily adaptable as a renewable biomass source to existing biodiesel manufacturing processes. Further, the remaining algal biomass may be converted to bio-ethanol, converted to bio-diesel, converted to methane, burned, or used as food for other organisms.

Another commercial purpose of significant import includes algae cultivation for the production of omega-3 oil, omega-6 oil, and axstasanthin (3,3'-dihydroxy-β-carotene-4,4'-dione) in pharmaceuticals, nutraceuticals, and food supplements.

Commercial acceptance of biomass products is dependent on a variety of factors such as, for example, cost to manufacture, cost to operate, reliability, durability, and scalability. Commercial acceptance of biomass products is also dependent on the ability to increase biomass product growth and recovery, while decreasing biomass production cost. Therefore, it may be desirable to have novel approaches for growing and harvesting biomass products including, for example, cell components such as lipids, proteins, vitamins, fatty acids, minerals, carotenoids, pigments, and the like.

Providing faster growth and producing high density cultures is critical to achieving the operational scale necessary for current environmental and industrial needs. Ideally, improving the speed of growth and increasing the density of a culture will require less production space and consequently will lower the cost of associated facilities.

In line with these reasons and others, the cultivation of algae in liquid suspension, rather than within the ground, allows greater access to the nutrient sources necessary for growth, i.e., water, $CO_2$, and minerals, and permits reducing the production space to a cost-effective footprint. Accordingly, considerable activity has been focused on efficiently growing photoautotrophic microorganisms in liquid suspension, and specifically to mass culture unicellular algae.

Algal yield can be restricted by the limited wavelength range of light energy capable of driving photosynthesis, between about 400-700 nm (nanometers), which is only about half of the total solar energy. Other factors, such as respiration requirements during dark periods, efficiency of absorbing sunlight, and other growth conditions can affect photosynthetic efficiencies in algal bioreactors. The net result is an overall photosynthetic efficiency that has been too low for economical large scale production. Thus, the need exists for a large scale production system that provides the user a cost-effective means of installation, operation and maintenance relative to production yields. It is desirable that such a system also increase photosynthesis to maximize production yield.

In order to produce optimal yields, algae need to have $CO_2$ in large quantities in the basins or bioreactors where they grow. In addition to $CO_2$, the growth rate of algae may benefit from exposure to other nutrients that are common in known plant fertilizers.

Furthermore, algae need effective control of light. To maximize the growth of photosynthetic organisms, light must be available at the right intensity, the right frequency, and without excessive heat. Excessive light intensity can limit growth by inducing photo-respiration or bleaching the pigments needed for efficient cell growth. In addition, light intensity or light frequency in excess of the culture requirements may result in heat build-up that can limit culture growth. These problems are readily apparent in production systems that rely solely on direct solar light as a driver of photosynthesis, such as in ponds and raceways. Solar light is subject to extreme diurnal and seasonal variability. In addition, cultures relying on direct solar light are subject to periodic heating from light intensities and spectra not immediately useable by the culture.

The ability to effectively control light for 24 hours per day encourages faster growth of biomass and secondary metabolites as well as continuous consumption of $CO_2$. This results in a more efficient use of facilities, enabling a smaller footprint for a given level of production. However, the use of artificial light has a cost that must be minimized for successful industrial application.

The two major obstacles that reduce the uniform delivery of light to a culture are turbidity and bio-filming. Turbidity occurs as a culture approaches a density where some of the organisms shade others from the light. Ensuring delivery of the appropriate amount of light to each organism becomes increasingly difficult as the density of the organisms in a culture increases. Turbidity within a culture results in some organisms receiving less light than they can use and non-productive absorption of light by other organisms. The absorption of excess light wastes energy and contributes to heat build-up.

Bio-filming is an extremely widespread problem that occurs when a microorganism adheres to a surface. Most microorganisms, including species in all three domains, i.e., bacteria, eukaryotes, and archaea, perform processes that result in adhesion to surfaces and to other microorganisms. In industrial applications, biofilms often clog or corrode pipes and surfaces. In photo-bioreactors a biofilm can form over a light-delivery surface, thereby reducing the intensity and changing the spectra of the light transmitted.

SUMMARY OF THE INVENTION

The invention relates to systems and methods for cultivating photoautotrophic microorganisms. The invention further relates to a photo-bioreactor system and method for growing and harvesting algae in a mass production environment.

DETAILED DESCRIPTION OF SEVERAL EMBODIMENTS

A photo-bioreactor system and method for growing and harvesting photosynthetic organisms is disclosed in various embodiments. However, one skilled in the relevant art will recognize that the various embodiments may be practiced without one or more of the specific details, or with other replacement and/or additional methods, materials, or components. In other instances, well-known structures, materials, or operations are not shown or described in detail to avoid obscuring aspects of various embodiments of the invention.

Similarly, for purposes of explanation, specific numbers, materials, and configurations are set forth in order to provide a thorough understanding of the invention. Nevertheless, the invention may be practiced without specific details. Furthermore, it is understood that the various embodiments shown in the figures are illustrative representations and are not necessarily drawn to scale.

Reference throughout this specification to "one embodiment" or "an embodiment" or variation thereof means that a particular feature, structure, material, or characteristic described in connection with the embodiment is included in at least one embodiment of the invention, but do not denote that they are present in every embodiment. Thus, the appearances of the phrases such as "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Nonetheless, it should be appreciated that, contained within the description are features which, notwithstanding the inventive nature of the general concepts being explained, are also of an inventive nature.

Figure 1:
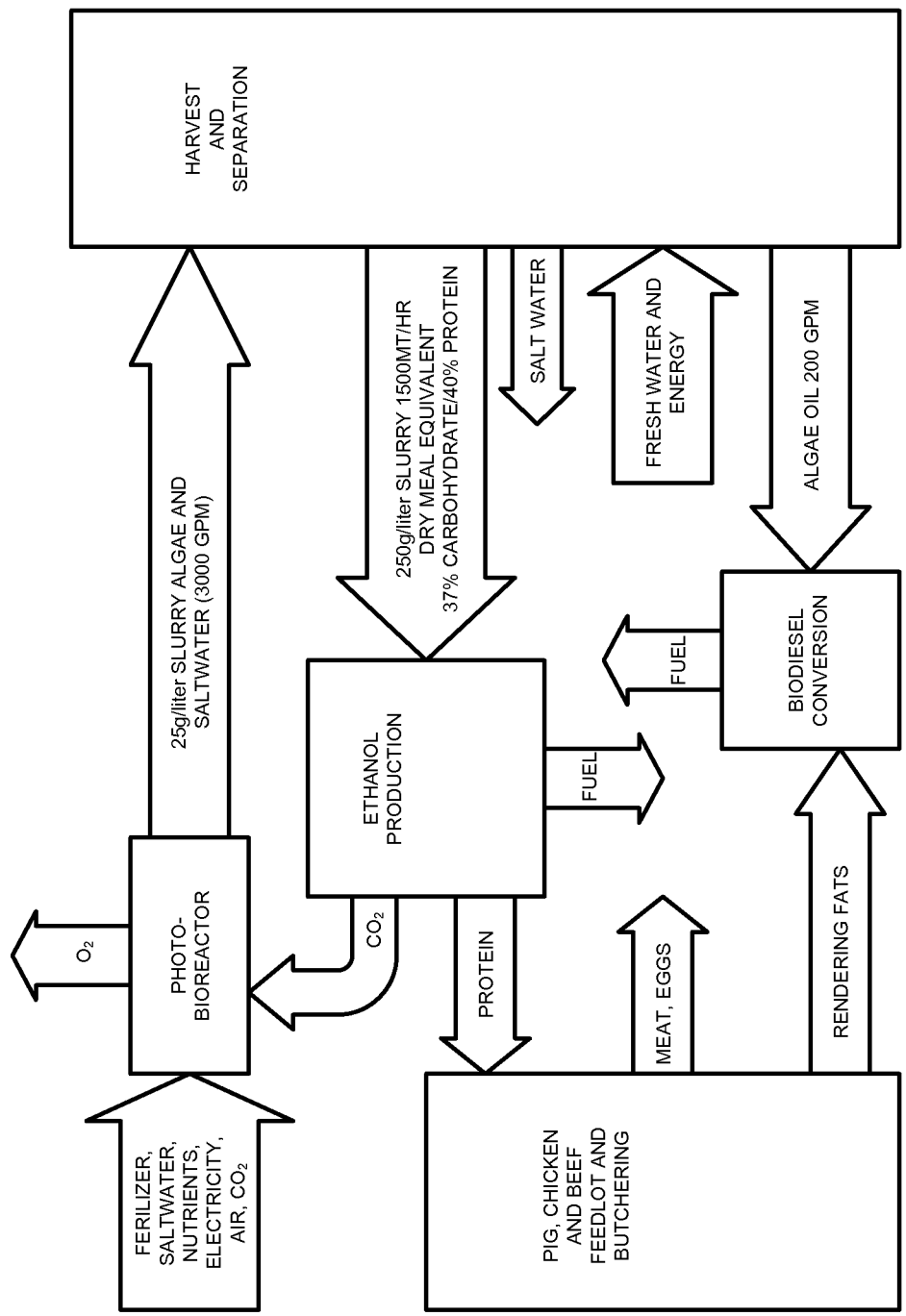
FIG. 1 provides a simplified schematic representation of an integrated system flow for algae cultivation for fuel production.

FIG. 1 provides an integration system flow illustrating the reactants and products involved in the integration of algae cultivation via a photo-bioreactor as a renewable biomass source in biofuel production.

Figure 2:
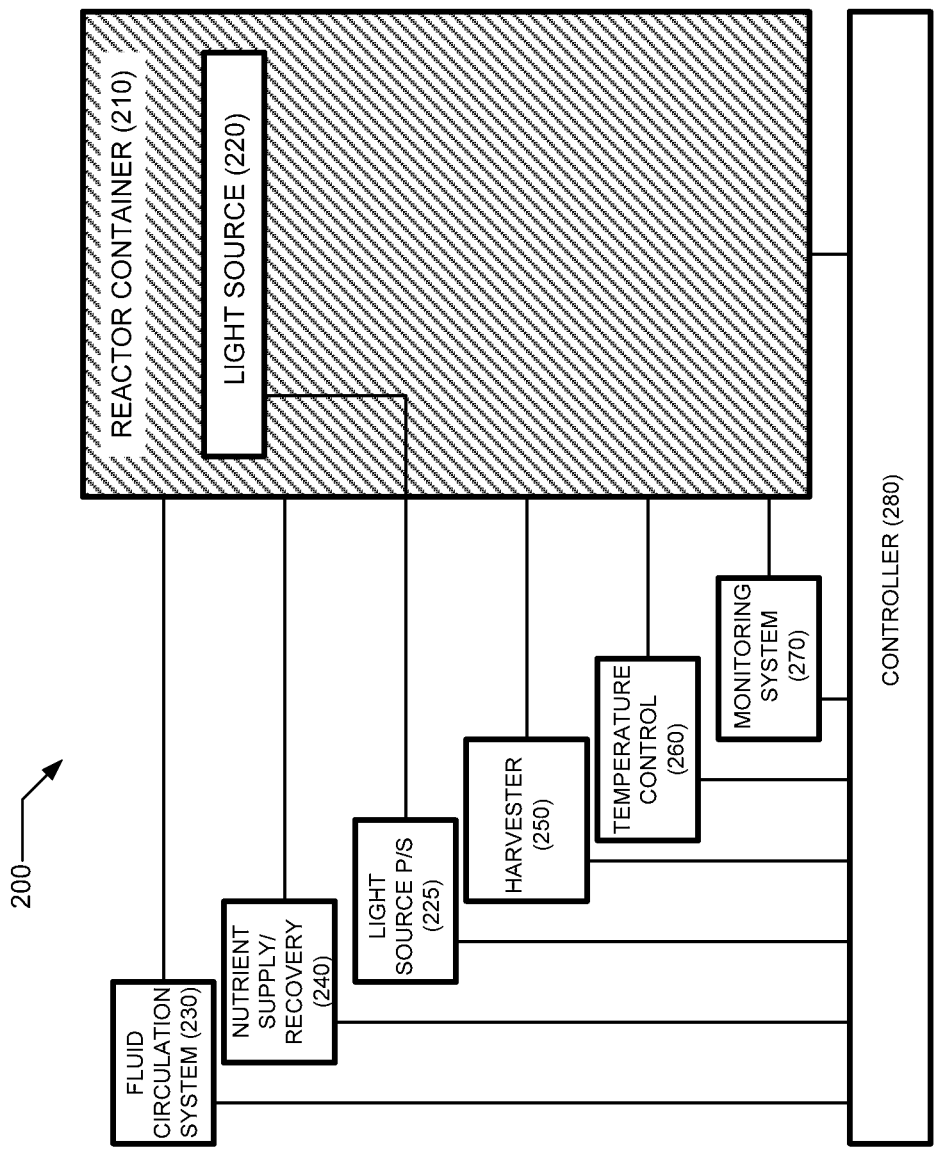
FIG. 2 illustrates a photo-bioreactor system according to an embodiment.

Referring now to FIG. 2, a photo-bioreactor system 200 is illustrated according to an embodiment. The photo-bioreactor system 200 includes a reactor container 210 having an interior space configured to receive and hold a fluid medium for growing photosynthetic organisms, a light source 220 coupled to the reactor container 210 and configured to illuminate at least some of the photosynthetic organisms in the fluid medium, and a fluid circulation system 230 coupled to the reactor container 210 and configured to force a continuous flow of the fluid medium through the reactor container 210. The fluid circulation system 230 may force the continuous flow of fluid medium through the reactor container 210 using a variety of pumping means including, but not limited to, a positive displacement pumping system (e.g., gear, rotary gear, rotary lobe, diaphragm, piston, screw, peristaltic, etc.), a rotodynamic pumping system (e.g., centrifugal, radial flow, axial flow, mixed flow, injector, ejector, eductor-jet, etc.), a buoyancy-driven pumping system (e.g., single-phase, multi-phase, etc.), or a gravity-driven pumping system (e.g., sloped container, etc.), or a combination of two or more thereof.

The photo-bioreactor system 200 further includes a nutrient supply/recovery system 240 for introducing and removing one or more nutrients to and from the reactor container 210, a light source power supply (P/S) 225 for providing power to the light source 220, a harvester 250 for extracting and harvesting the photosynthetic organisms, a temperature control system 260 for controlling a temperature of the light source 220 and/or the fluid medium, a monitoring system 270 for providing instrumentation and measuring process performance, and a control system 280 for controlling the photo-bioreactor system 200 and its various components.

Figure 3:
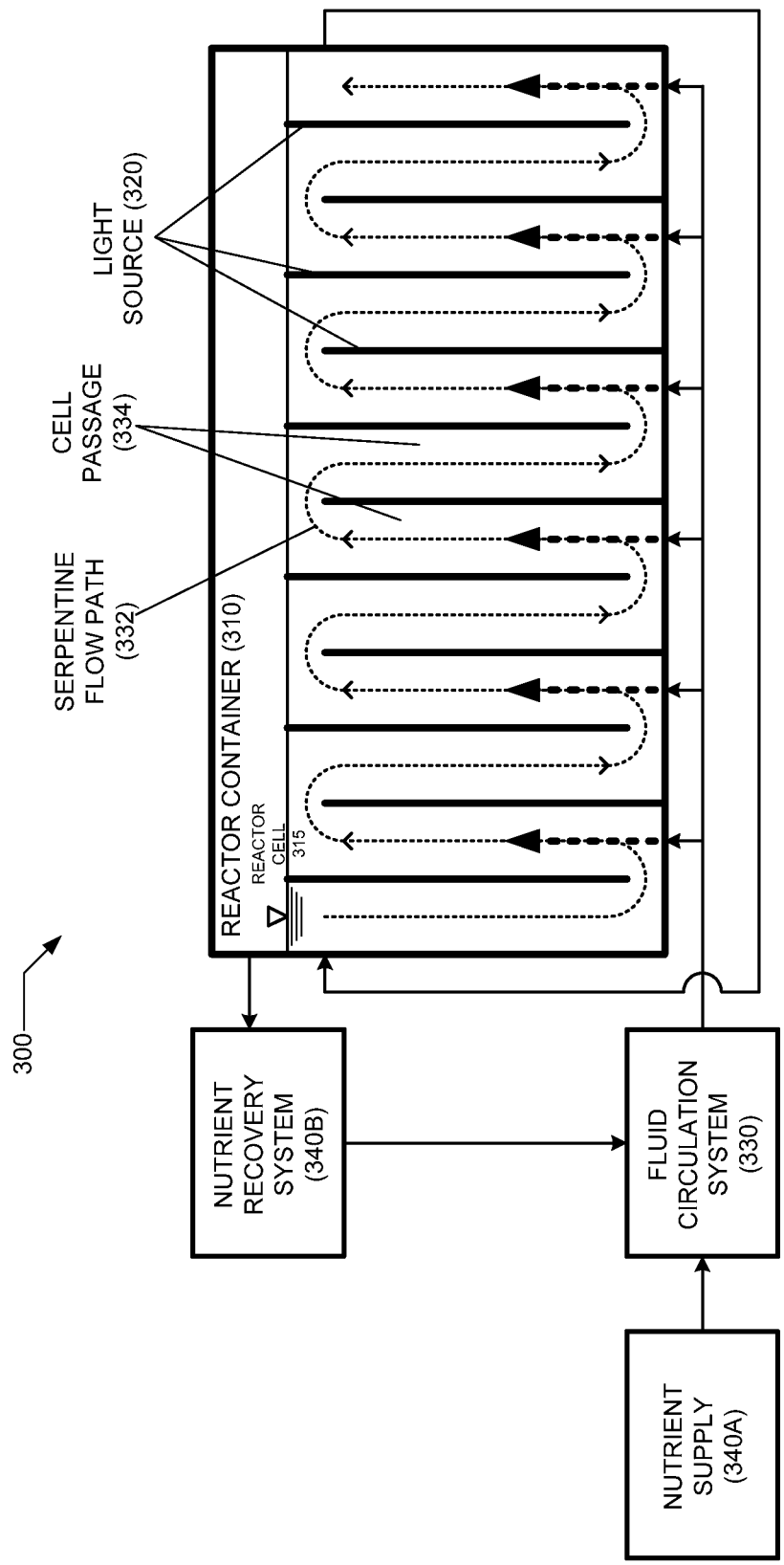
FIG. 3 illustrates a photo-bioreactor system according to another embodiment.

Referring now to FIG. 3, a photo-bioreactor system 300 is illustrated according to an embodiment. The photo-bioreactor system 300 includes a reactor container 310 having an interior space configured to receive and hold a fluid medium for growing photosynthetic organisms, a light source 320 coupled to the reactor container 310 and configured to illuminate at least some of the photosynthetic organisms in the fluid medium, and a fluid circulation system 330 coupled to the reactor container 310 and configured to force a continuous flow of the fluid medium through the reactor container 310.

The light source 320 comprises at least one light-emitting panel extending into the reactor container 310 and dividing the interior space of the reactor container 310 into a plurality of cell passages 334, wherein the at least one light-emitting panel has a first light-emitting surface and a second light-emitting surface on opposing sides of the light-emitting panel.

The fluid circulation system 330 forces the continuous flow which follows a serpentine flow path 332 that includes a flow path segment extending along the first light-emitting surface, a flow path segment passing around a distal end of the at least one light-emitting panel, and a flow path segment extending along the second light-emitting surface.

The photo-bioreactor 300 further includes a nutrient supply system 340A and a nutrient recovery system 340B.

The reactor container 310 may include one or more reactor cells 315. As shown in FIG. 3, at least one of the plurality of cell passages 334 comprises a uniform cell passage having a cross-sectional area that is substantially constant along at least a portion of the serpentine flow path 332. The at least one of the plurality of cell passages 334 is characterized by a spacing between adjacent light-emitting panels that is substantially constant in dimension along a direction of the continuous flow.

Figure 4:
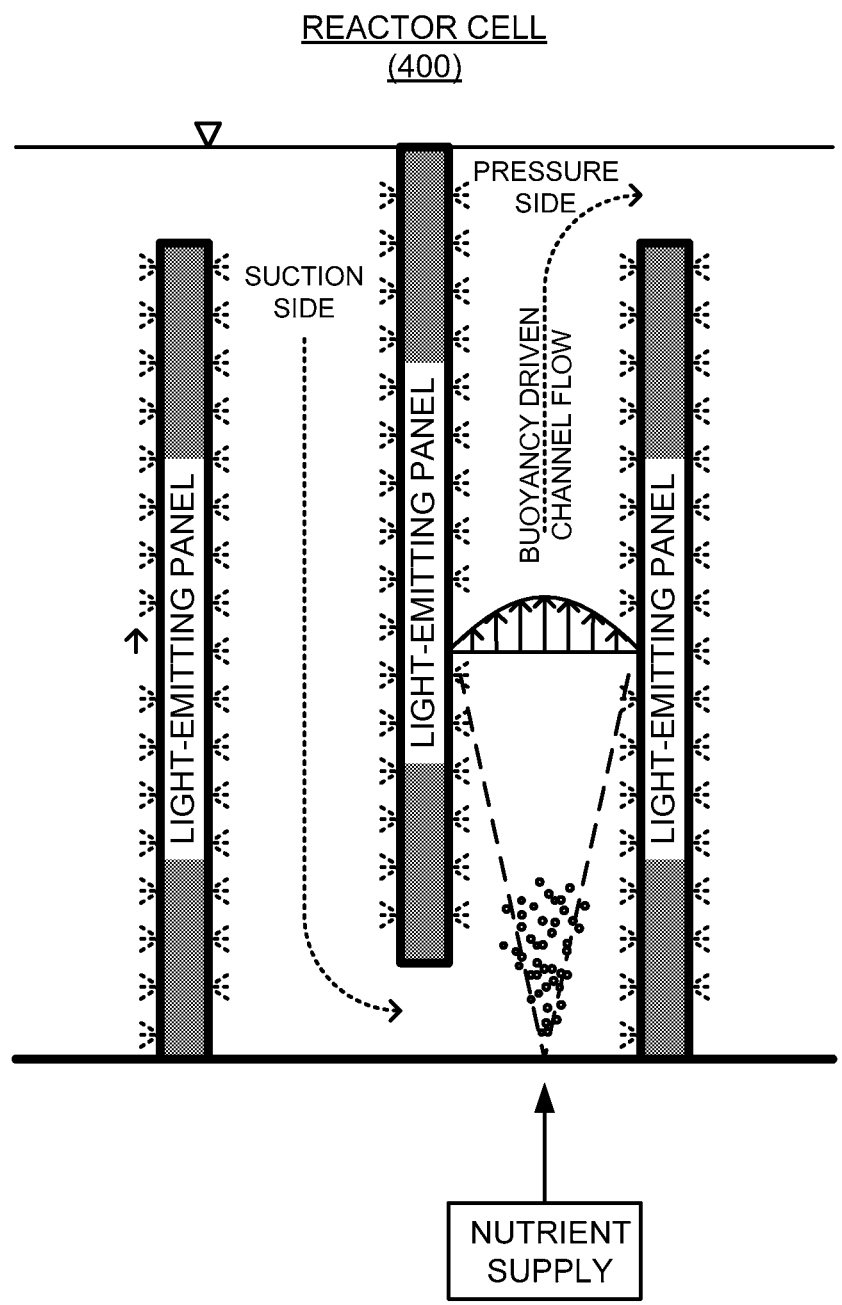
FIG. 4 provides an exploded view of a cell passage in a photo-bioreactor system according to an embodiment.

FIG. 4 provides an exploded view of a cell passage in a photo-bioreactor system according to an embodiment. A nutrient supply system or other system may introduce a fluid into a cell passage of the photo-bioreactor system to generate a buoyancy-driven channel flow through the at least one cell passage. The buoyancy-driven channel flow may include injection of a positively buoyant fluid (i.e., fluid density less than the density of the fluid medium) or a negatively buoyant fluid (i.e., fluid density greater than the density of the fluid medium). For example, a buoyancy-driven channel flow may be generated via injection of a positively buoyant fluid, such as a gas (e.g., $CO_2$), at a bottom of the reactor container. The injected gas (bubbles) rise vertically between vertically arranged light-emitting panels causing an upward flow on a pressure side of a light-emitting panel and drawing fluid medium from a suction side of the light-emitting panel.

Figure 5:
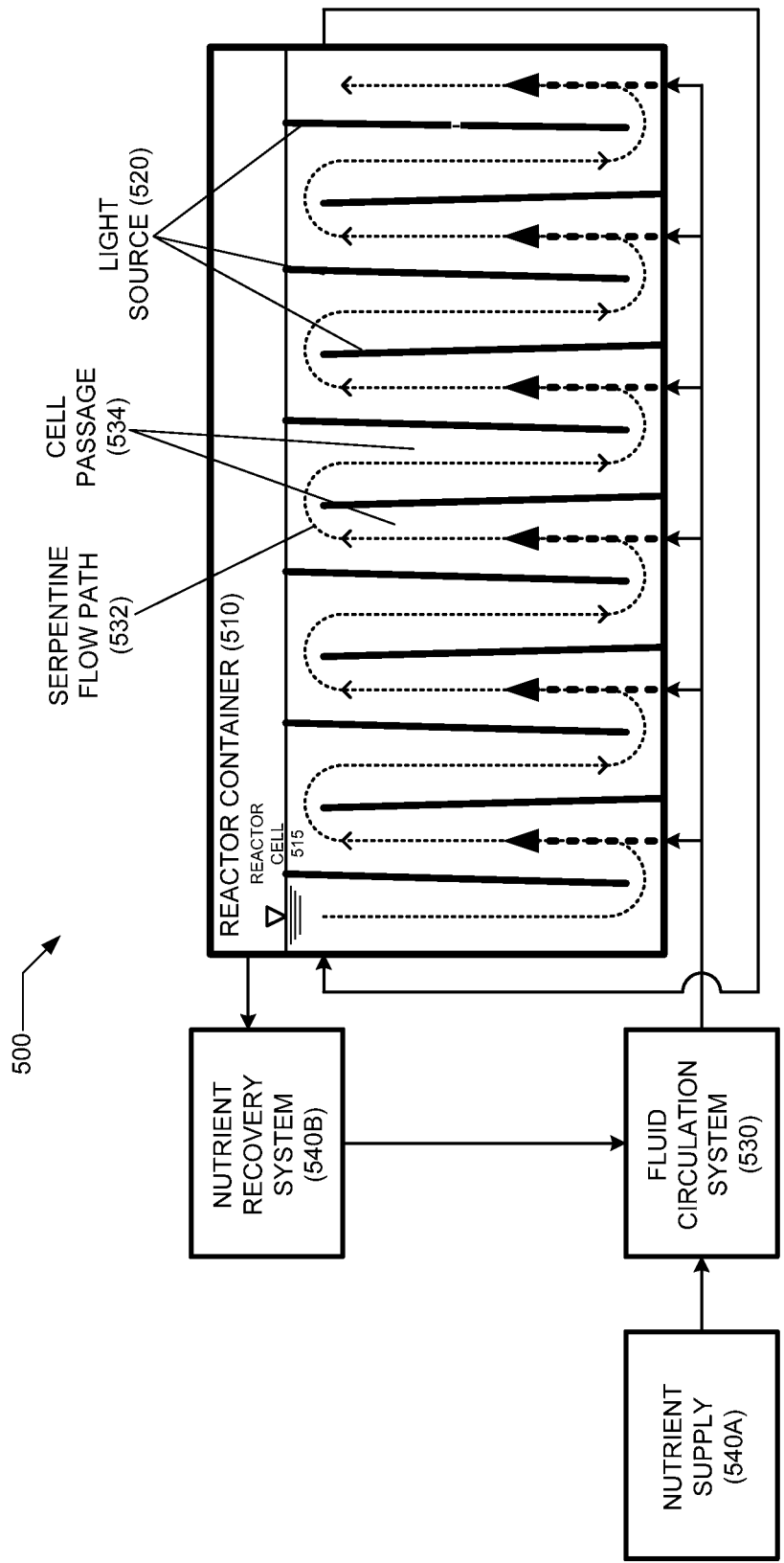
FIG. 5 illustrates a photo-bioreactor system according to another embodiment.

Referring now to FIG. 5, a photo-bioreactor system 500 is illustrated according to an embodiment. The photo-bioreactor system 500 includes a reactor container 510 having an interior space configured to receive and hold a fluid medium for growing photosynthetic organisms, a light source 520 coupled to the reactor container 510 and configured to illuminate at least some of the photosynthetic organisms in the fluid medium, and a fluid circulation system 530 coupled to the reactor container 510 and configured to force a continuous flow of the fluid medium through the reactor container 510.

The light source 520 comprises at least one light-emitting panel extending into the reactor container 510 and dividing the interior space of the reactor container 510 into a plurality of cell passages 534, wherein the at least one light-emitting panel has a first light-emitting surface and a second light-emitting surface on opposing sides of the light-emitting panel.

The fluid circulation system 530 forces the continuous flow which follows a serpentine flow path 532 that includes a flow path segment extending along the first light-emitting surface, a flow path segment passing around a distal end of the at least one light-emitting panel, and a flow path segment extending along the second light-emitting surface.

The photo-bioreactor 500 further includes a nutrient supply system 540A and a nutrient recovery system 540B.

The reactor container 510 may include one or more reactor cells 515. As shown in FIG. 5, at least one of the plurality of cell passages 534 comprises a convergent cell passage having a cross-sectional area that decreases along at least a portion of the serpentine flow path 532. The at least one of the plurality of cell passages 534 is characterized by a spacing between adjacent light-emitting panels that decreases in dimension along a direction of the continuous flow. The area reduction may stabilize the channel flow between adjacent light-emitting panels.

Figure 6:
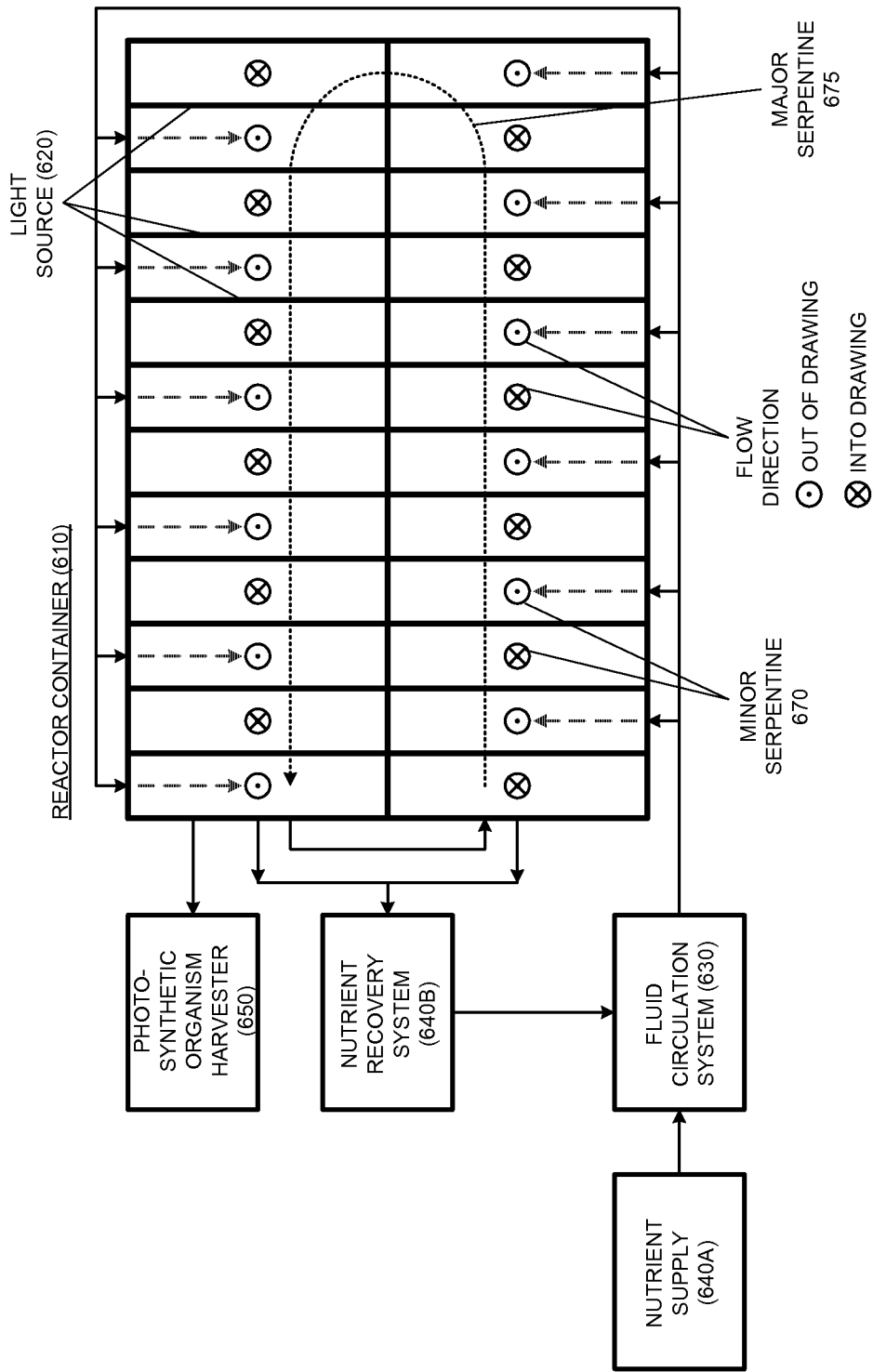
FIG. 6 illustrates a photo-bioreactor system according to another embodiment.

Referring now to FIG. 6, a plan view of a photo-bioreactor system 600 is illustrated according to an embodiment. The photo-bioreactor system 600 includes a reactor container 610 having an interior space configured to receive and hold a fluid medium for growing photosynthetic organisms, a light source 620 coupled to the reactor container 610 and configured to illuminate at least some of the photosynthetic organisms in the fluid medium, and a fluid circulation system 630 coupled to the reactor container 610 and configured to force a continuous flow of the fluid medium through the reactor container 610.

As depicted in FIG. 6, the photo-bioreactor system 600 may be arranged along a serpentine racetrack, one lobe of which is illustrated. The continuous flow of fluid medium follows a serpentine flow path between light-emitting panels along a minor serpentine 670 arranged, for example, in a vertical plane, and the continuous flow of fluid medium follows a serpentine flow path through racetrack laps along a major serpentine 675 arranged, for example, in a horizontal plane.

The photo-bioreactor 600 also includes a photo-synthetic organism harvester 650 coupled to each lap of the serpentine racetrack. The photo-bioreactor 600 further includes a nutrient supply system 640A and a nutrient recovery system 640B.

Figure 7:
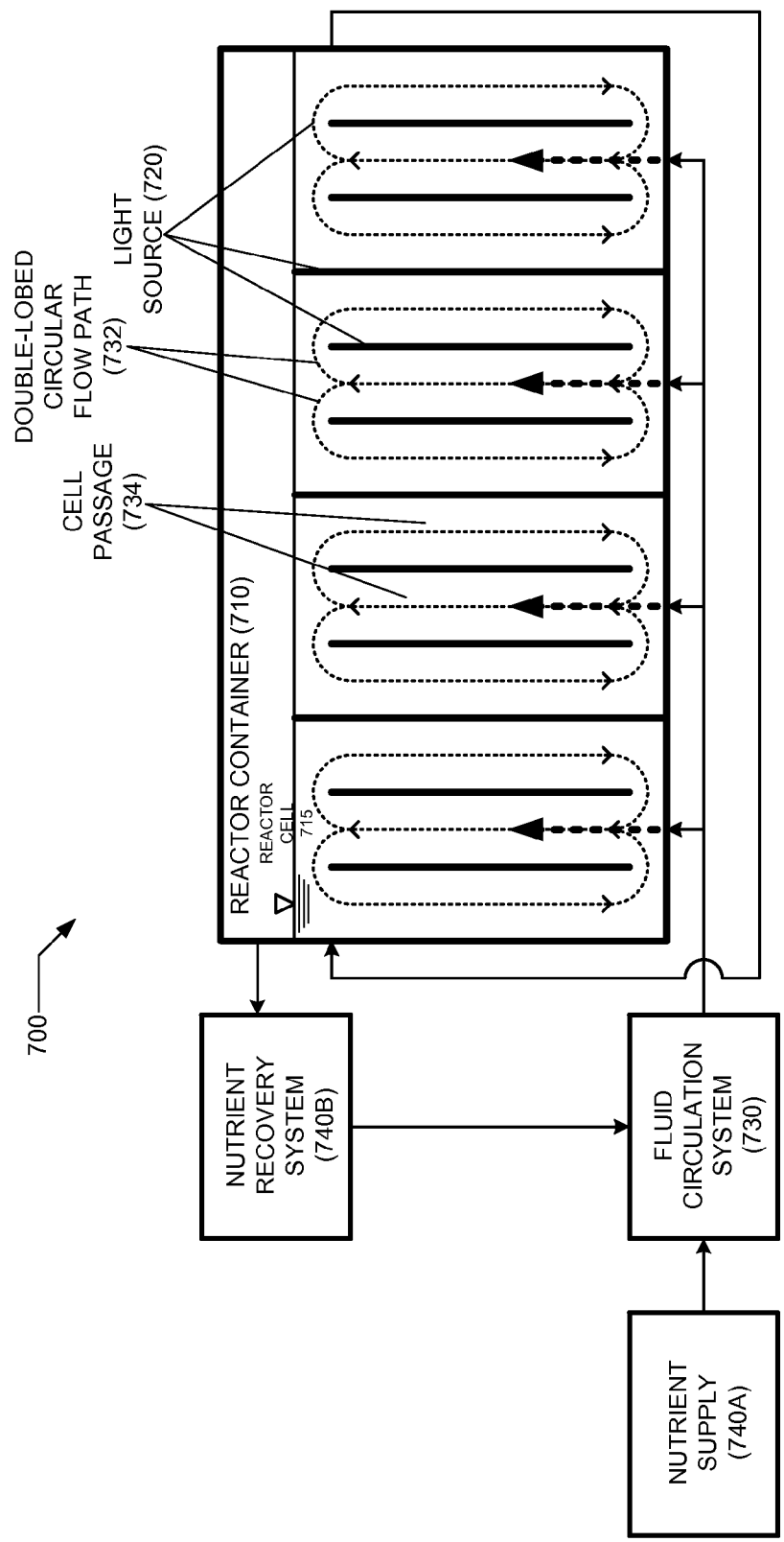
FIG. 7 illustrates a photo-bioreactor system according to another embodiment.

Referring now to FIG. 7, a photo-bioreactor system 700 is illustrated according to an embodiment. The photo-bioreactor system 700 includes a reactor container 710 having an interior space configured to receive and hold a fluid medium for growing photosynthetic organisms, a light source 720 coupled to the reactor container 710 and configured to illuminate at least some of the photosynthetic organisms in the fluid medium, and a fluid circulation system 730 coupled to the reactor container 710 and configured to force a continuous flow of the fluid medium through the reactor container 710. The reactor container 710 may include one or more reactor cells 715.

The light source 720 comprises at least one light-emitting panel extending into the reactor container 710 and dividing the interior space of the reactor container 710 into a plurality of cell passages 734, wherein the at least one light-emitting panel has a first light-emitting surface and a second light-emitting surface on opposing sides of the light-emitting panel.

The fluid circulation system 730 forces the continuous flow which follows a double-lobed circular flow path 732.

The photo-bioreactor 700 further includes a nutrient supply system 740A and a nutrient recovery system 740B.

Figure 8:
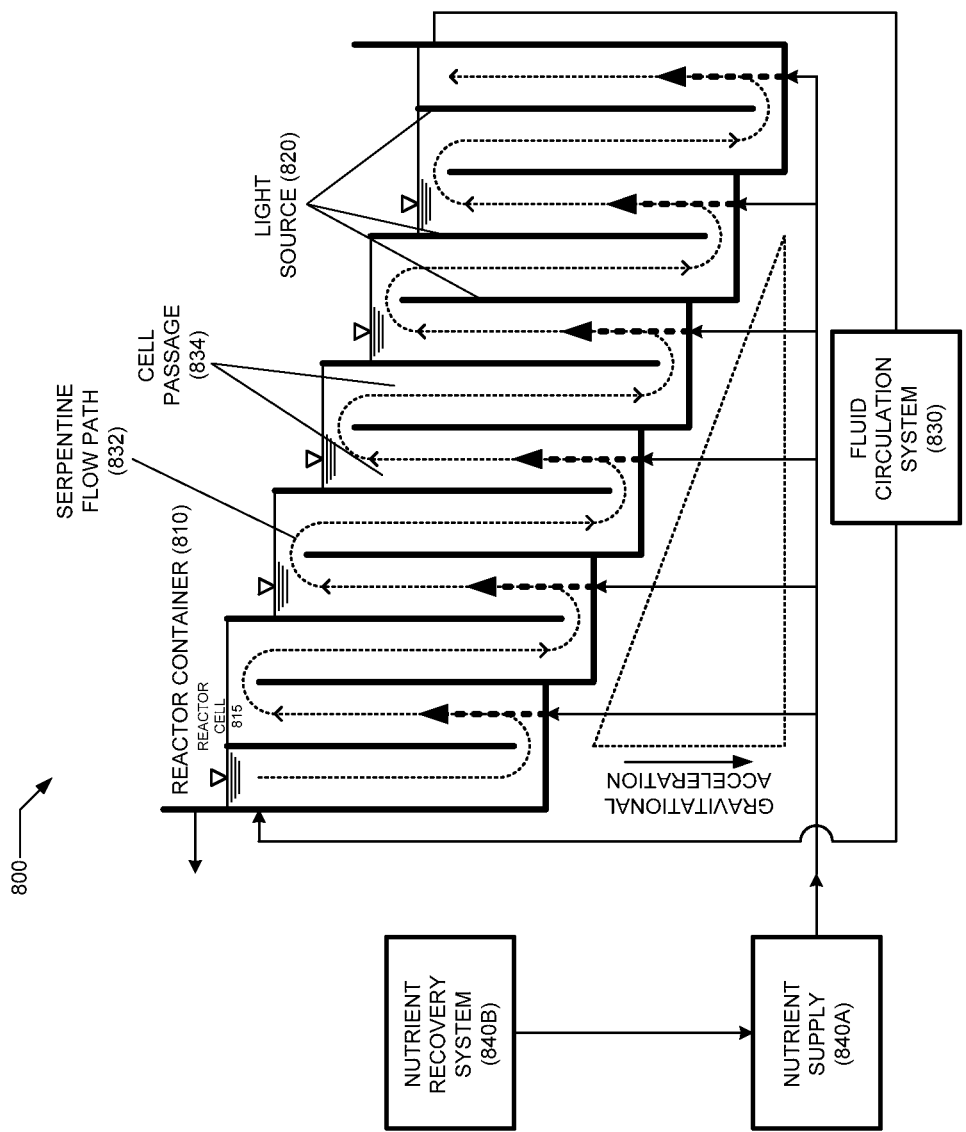
FIG. 8 illustrates a photo-bioreactor system according to another embodiment.

Referring now to FIG. 8, a photo-bioreactor system 800 is illustrated according to an embodiment. The photo-bioreactor system 800 includes a reactor container 810 having an interior space configured to receive and hold a fluid medium for growing photosynthetic organisms, a light source 820 coupled to the reactor container 810 and configured to illuminate at least some of the photosynthetic organisms in the fluid medium, and a fluid circulation system 830 coupled to the reactor container 810 and configured to force a continuous flow of the fluid medium through the reactor container 810.

The light source 820 comprises at least one light-emitting panel extending into the reactor container 810 and dividing the interior space of the reactor container 810 into a plurality of cell passages 834, wherein the at least one light-emitting panel has a first light-emitting surface and a second light-emitting surface on opposing sides of the light-emitting panel.

The fluid circulation system 830 forces the continuous flow which follows a serpentine flow path 832 that includes a flow path segment extending along the first light-emitting surface, a flow path segment passing around a distal end of the at least one light-emitting panel, and a flow path segment extending along the second light-emitting surface. The continuous flow is driven by gravity through the reactor container 810, and the fluid medium is returned from a position of lower static head to a position of higher static head using a pumping system, such as a positive displacement pump or rotodynamic pump. The pumping system may include a low shear pump. For example, the pumping system may include an Archimedes' screw pump.

The photo-bioreactor 800 further includes a nutrient supply system 840A and a nutrient recovery system 840B.

The reactor container 810 may include one or more reactor cells 815 stepped downward along a slope to allow gravity to assist pumping and circulation, as discussed above. The slope may be linear or non-linear. Additionally, the slope may be altered using an actuator configured to adjust the elevation of each reactor cell 815, or tilt the reactor container 810.

As shown in FIG. 8, at least one of the plurality of cell passages 834 comprises a uniform cell passage having a cross-sectional area that is substantially constant along at least a portion of the serpentine flow path 832. The at least one of the plurality of cell passages 834 is characterized by a spacing between adjacent light-emitting panels that is substantially constant in dimension along a direction of the continuous flow. Alternatively, at least one of the plurality of cell passages 834 comprises a convergent cell passage having a cross-sectional area that decreases along at least a portion of the serpentine flow path 832.

Figure 9A:
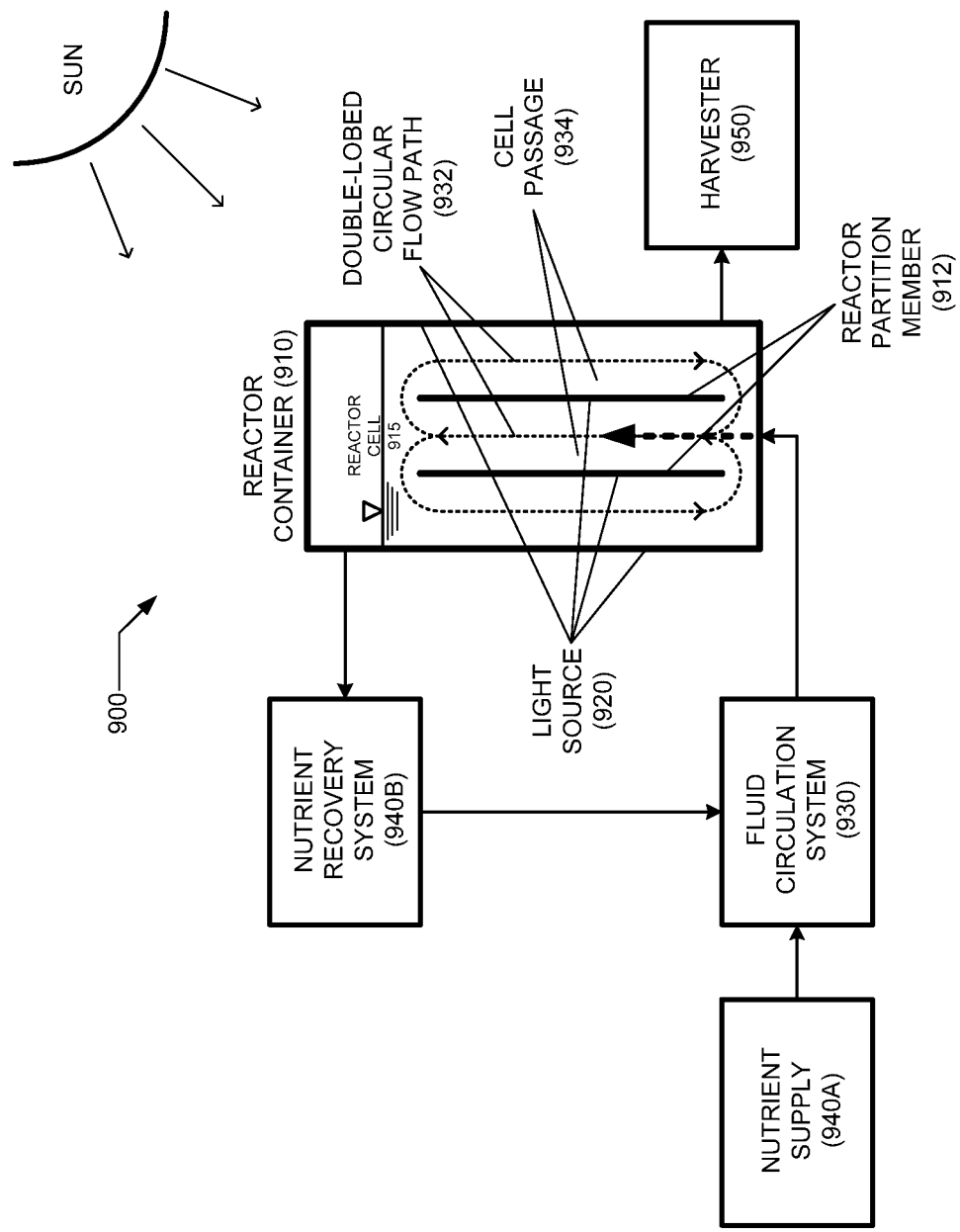
FIG. 9A illustrates a photo-bioreactor system according to yet another embodiment.

Referring now to FIG. 9A, a photo-bioreactor system 900 is illustrated according to an embodiment. The photo-bioreactor system 900 includes a reactor container 910 having a reactor partition member 912 and an interior space configured to receive and hold a fluid medium for growing photosynthetic organisms, a light source 920 coupled to the reactor container 910 and/or the reactor partition member 912, and configured to illuminate at least some of the photosynthetic organisms in the fluid medium, and a fluid circulation system 930 coupled to the reactor container 910 and configured to force a continuous flow of the fluid medium through the reactor container 910. The reactor container 910 may include one or more reactor cells 915. The reactor partition member 912 divides the interior space of the reactor container 910 into a plurality of cell passages 934.

The light source 920 comprises at least one cylindrical light-emitting panel coupled to an inner surface and/or an outer surface of the reactor container 910, and/or an inner surface and/or an outer surface of the inner cylinder. The at least one cylindrical light-emitting panel has at least one light-emitting surface. Further, the at least one cylindrical light-emitting panel may include a flexible printed circuit board (PCB) with light-emitting devices formed thereon.

The fluid circulation system 930 forces the continuous flow which follows a double-lobed circular flow path 932.

The photo-bioreactor 900 further includes a nutrient supply system 940A, a nutrient recovery system 940B, and a harvester 950.

Figure 9C:
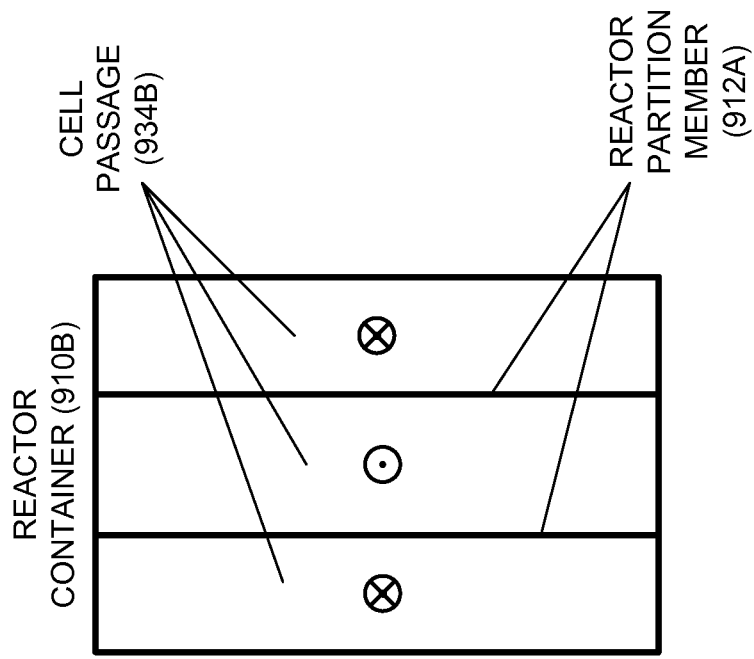
FIGS. 9B and 9C illustrate a top view of a bioreactor system according to yet other embodiments.
Figure 9B:
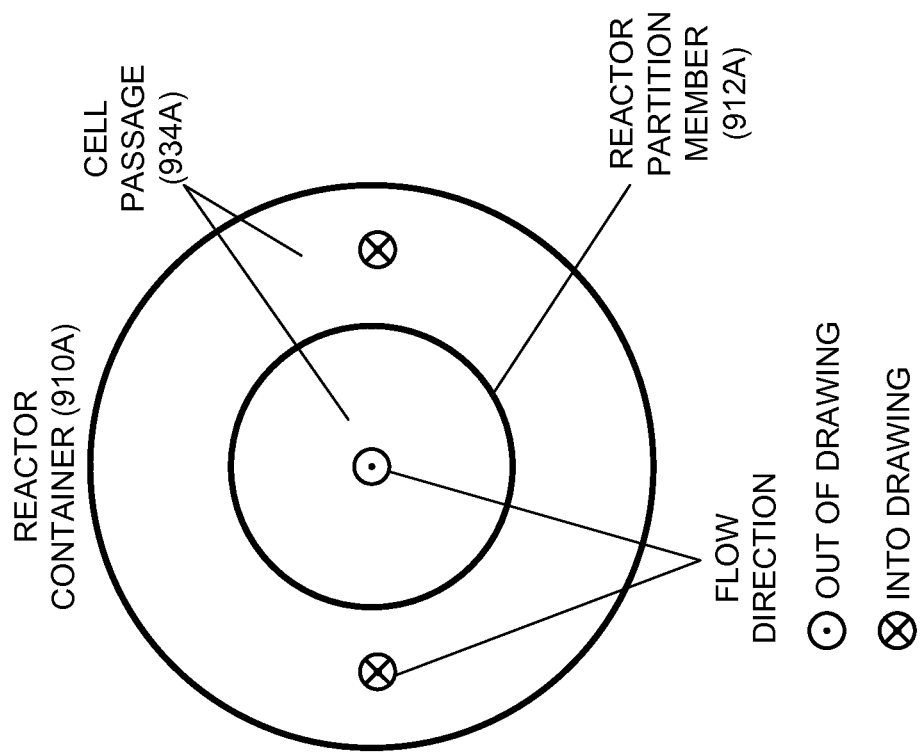

FIG. 9B provides a top view of a cylindrical reactor container 910A having a cylindrical reactor partition member 912A that divides the cylindrical interior space into a plurality of cell passages 934A having a central cell passage and an annular cell passage. The continuous flow of fluid medium may follow a double-lobed circular flow path or toroidal flow path. The cylindrical reactor container 910A may include a plurality of cylindrical reactor partition members 912A.

FIG. 9C provides a top view of a rectangular reactor container 910B having a rectangular reactor partition member 912B that divides the rectangular interior space into a plurality of cell passages 934B having an inner cell passage and an outer cell passage. The continuous flow of fluid medium may follow a double-lobed circular flow path. The rectangular reactor container 910B may include a plurality of rectangular reactor partition members 912B.

In alternative embodiments, any one of the photo-bioreactor systems (200, 300, 500, 600, 700, 800, 900) depicted in FIGS. 2, 3, and 5-9 may be placed in direct exposure to the sun. During daylight hours, direct sunlight may complement and/or replace in part any artificial lighting used.

In alternative embodiments, any component of the photo-bioreactor systems (200, 300, 500, 600, 700, 800, 900)

depicted in FIGS. 2, 3, and 5-9 may be fabricated from transparent and/or opaque materials.

Light-Emitting Panel

Figures 10A, 10B:
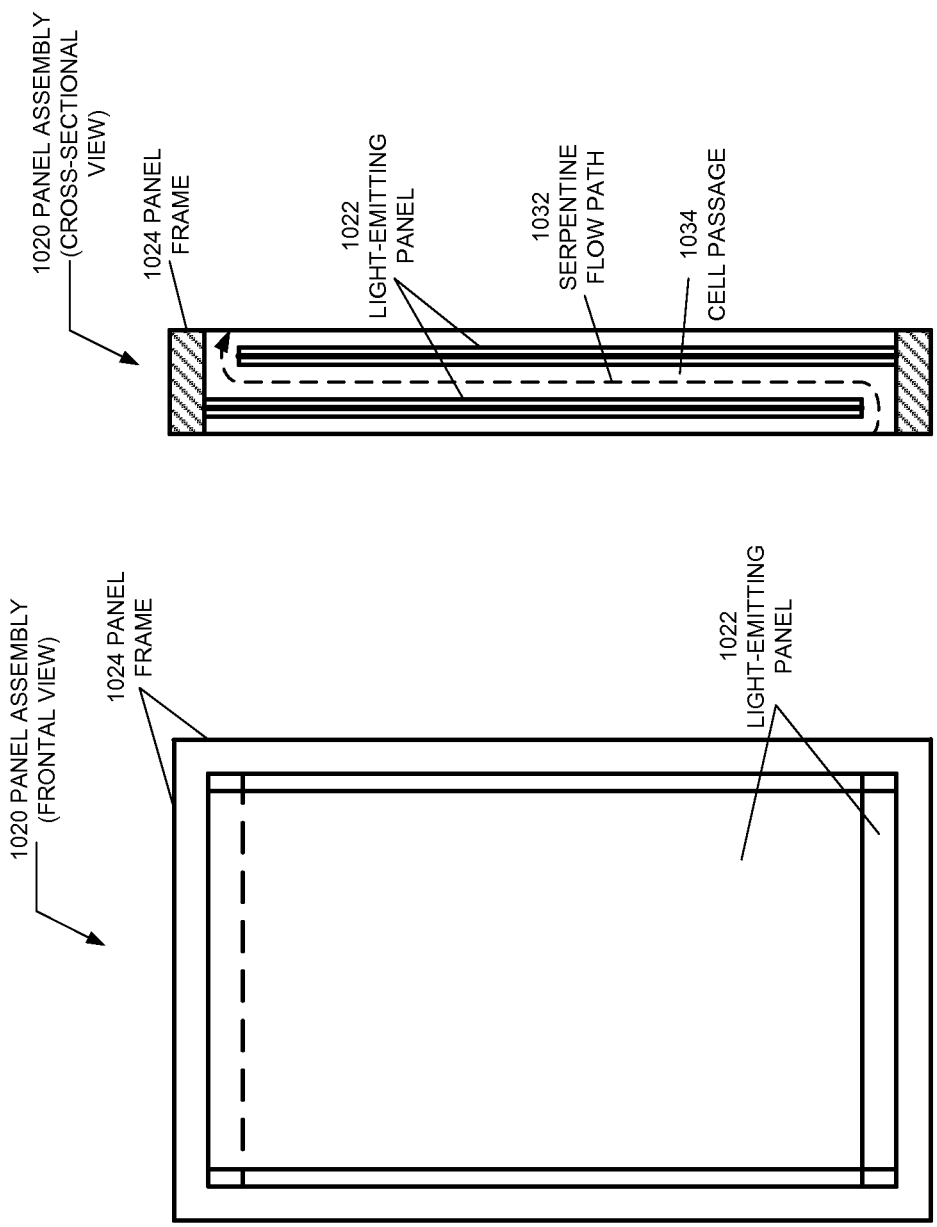
FIGS. 10A and 10B provide a frontal view and a cross-sectional view of a light-emitting panel assembly according to an embodiment.

A light-emitting panel emits light and may further cool and/or heat the fluid medium. The light-emitting panel may be positioned in the photo-bioreactor system as described earlier (see FIGS. 3 through 8), and it is depicted in greater detail in FIGS. 10A, 10B, and 11. FIG. 10A provides a frontal view of a panel assembly 1020 that includes a pair of light-emitting panels 1022 arranged in a panel frame 1024. FIG. 10B provides a cross-sectional view of panel assembly 1020, and illustrates a continuous flow of fluid medium moving along a serpentine flow path 1032 through a cell passage 1034. Each panel frame 1024 may be replacably inserted into and out of a reactor container. Alternatively, the reactor container may be constructed in a modular fashion by assembling and arranging panel frames adjacent to one another.

Figure 11:
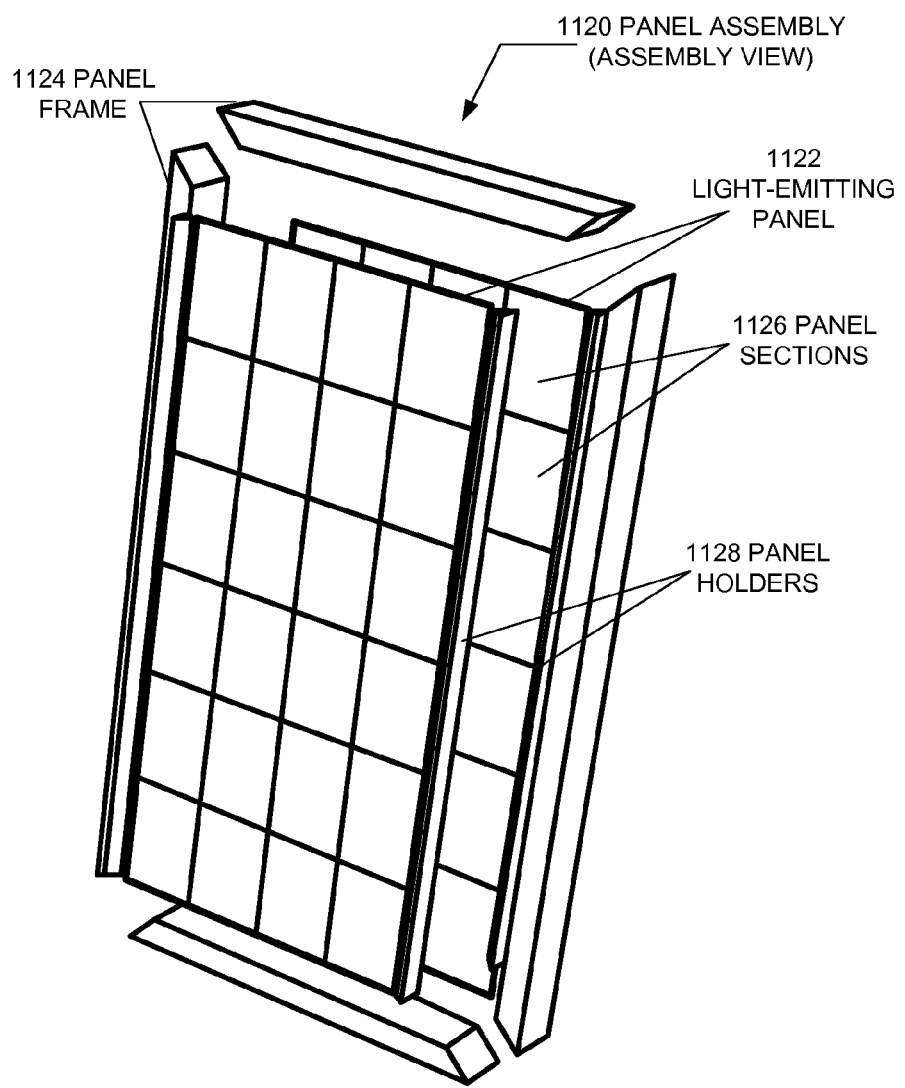
FIG. 11 illustrates an assembly view of a light-emitting panel assembly according to another embodiment.

Additionally, as shown in FIG. 11 in an assembly view, a panel assembly 1120 may be constructed by arranging a pair of light-emitting panels 1122 in a panel frame 1124, wherein each light-emitting panel is affixed to the panel frame 1124 using one or more panel holders 1028. Further, each light-emitting panel 1122 may be comprised of multiple panel sections 1126 that are arranged to form a panel and that are separated to allow for refitting, refurbishing, and/or maintaining individual panel sections 1126. This modular design permits maintenance of a section without the requirement of replacing an entire light-emitting panel 1122.

Each panel section may possess electrical connection, pneumatic connection, and/or fluid connection including but not limited to the following:

(1) Cooling and/or heating fluid connection. Temperature control of each light-emitting panel and/or panel section, including both heating and/or cooling, may proceed during growth of photosynthetic organisms. Additionally, temperature control of each light-emitting panel and/or panel section, including both heating and/or cooling, may vary during growth of photosynthetic organisms. For example, heating may be necessary during start-up, while cooling may be necessary during growth cycles. Each panel and/or panel section may include inlet and outlet fluid connection for flowing a heat transfer fluid to heat and/or cool each panel and/or panel section, as well as the fluid medium within which the photosynthetic organisms are suspended and grown.

(2) Electrical connection for instrumentation. The instrumentation electrical connection may include a multiple wire cable, having any of a number of digital cables and/or fiber optic cables. The instrumentation electrical connection may facilitate transmitting and/or receiving: (a) a timing pulse for light emission; (b) an optical detector output (direct or digitized on-board the panel and provided to the control system); (c) a temperature control signal (including both fluid medium and/or critical on-board temperature data that are critical for efficient light conversion); (d) an electrical current feedback on individual arrays of LEDs, LED lasers, or micro-cavity discharges; (e) an optical detector output on individual arrays of LEDs, LED lasers, or micro-cavity discharges to detect degradation of light emission from the respective light source; and (f) an electrical connection for power that may be delivered as direct current (DC) or alternating current (AC), and converted on-board to voltages sufficient to drive each array of light-emitting devices.

The light source may include a variety of devices. As described above, the light source includes one or more light-emitting panels immersed, at least in part, within the fluid medium that photosynthetic organisms are suspended and grown. The light source may include sunlight and/or artificial light emitted by the one or more light-emitting panels. The light source may include visible light, e.g., about 380 nm to about 780 nm. Alternatively, the light source may include visible light, e.g., about 440 nm to about 660 nm. The light may be artificially generated in-situ (i.e., on-board each light-emitting panel). Alternatively, the light may be generated ex-situ and coupled to each light-emitting panel via fiber optic cable. In the latter, fiber optic coupled light may suffer from loss in intensity and may provide greater expense.

The light emission may include, overlap, and/or coincide with the absorption spectra for chlorophyll. For example, the light emission may include, overlap, and/or coincide with the absorption spectra for chlorophyll A and/or B (see FIG. 14). The inventors suspect that either A or B separately are optimum for algae growth, or the inventors suspect that some parts of the spectra are more efficient than others at supporting growth. Similarly, different parts of the spectra may be able to stimulate the growth of a certain component of the cell, e.g., more oil, more omega-3 oil, or more omega-6 oil, etc. It is believed that the A and B chlorophyll species, being different materials, may have different timing requirements for light and dark phases, and may require different pulse dark times and be optimized for growth at different light intensities and pulse lengths.

The light source may provide light emission using a light-emitting diode (LED), an LED laser, and/or a microcavity plasma discharge. The light source may include a plurality of light-emitting devices. The light-emitting devices may be arranged in arrays. For example, a light-emitting panel may include multiple arrays of plural light-emitting devices. Several options are provided below:

Light-emitting diodes (LEDs)—LEDs have a broad spectral distribution of a few nanometers, and may possess a bandwidth similar to the bandwidth of chlorophyll A and B lines. Standard LEDs are not very efficient in that the wall plug efficiency is about 15-20%. However, state-of-the-art LEDs, such as those commercially available from Osram Opto Semiconductors, may be about 40% efficient. Proper tuning of the materials may generate an efficient LED for both red and possibly blue/green chlorophyll A and B lines.

LED lasers—LED lasers are relatively narrow in bandwidth, i.e., usually about 1 nm. As an example, an array of LED lasers may be used to produce a spectral distribution that matches the absorption spectra of chlorophyll in frequency and in number to match the intensity of absorption.

Deep blue LED—Deep blue LEDs are used for white light LEDs that are designed for area lighting. The deep blue line emission is converted to a range of frequencies using a mixture of phosphors. Different phosphors produce a different spectral emission. Red phosphors may be chosen to convert blue light to red light for providing an emission spectra match to chlorophyll absorption spectra. Red phosphors are notoriously inefficient, while blue and green phosphors are very efficient. This observation may promote a user to drive photo-induced growth of algae by using the blue and green absorption spectra. The inventors suspect that these lines are more efficient than the red spectra in promoting growth. Blue LEDs are very efficient at about 75% wall plug efficiency, while the conversion of a good phosphor is about 30% wall plug efficiency, thus, leaving the overall conversion efficiency at about 25%. The phosphor may comprise an oxide, a nitride, an oxynitride, a phosphide, a sulfide, a selenide, a halide, or a silicate of zinc, cadmium, manganese, aluminum, silicon, or rare earth metal, for example.

Micro-cavity plasma discharge—Micro-cavity plasma discharge, hereinafter micro-discharge, is described with reference to FIGS. 12A through 12C. An exemplary micro-discharge device is described in U.S. Pat. No. 7,385,350, entitled "ARRAYS OF MICROCAVITY PLASMA DEVICES WITH DIELECTRIC ENCAPSULATED ELECTRODES".

Figure 12A:
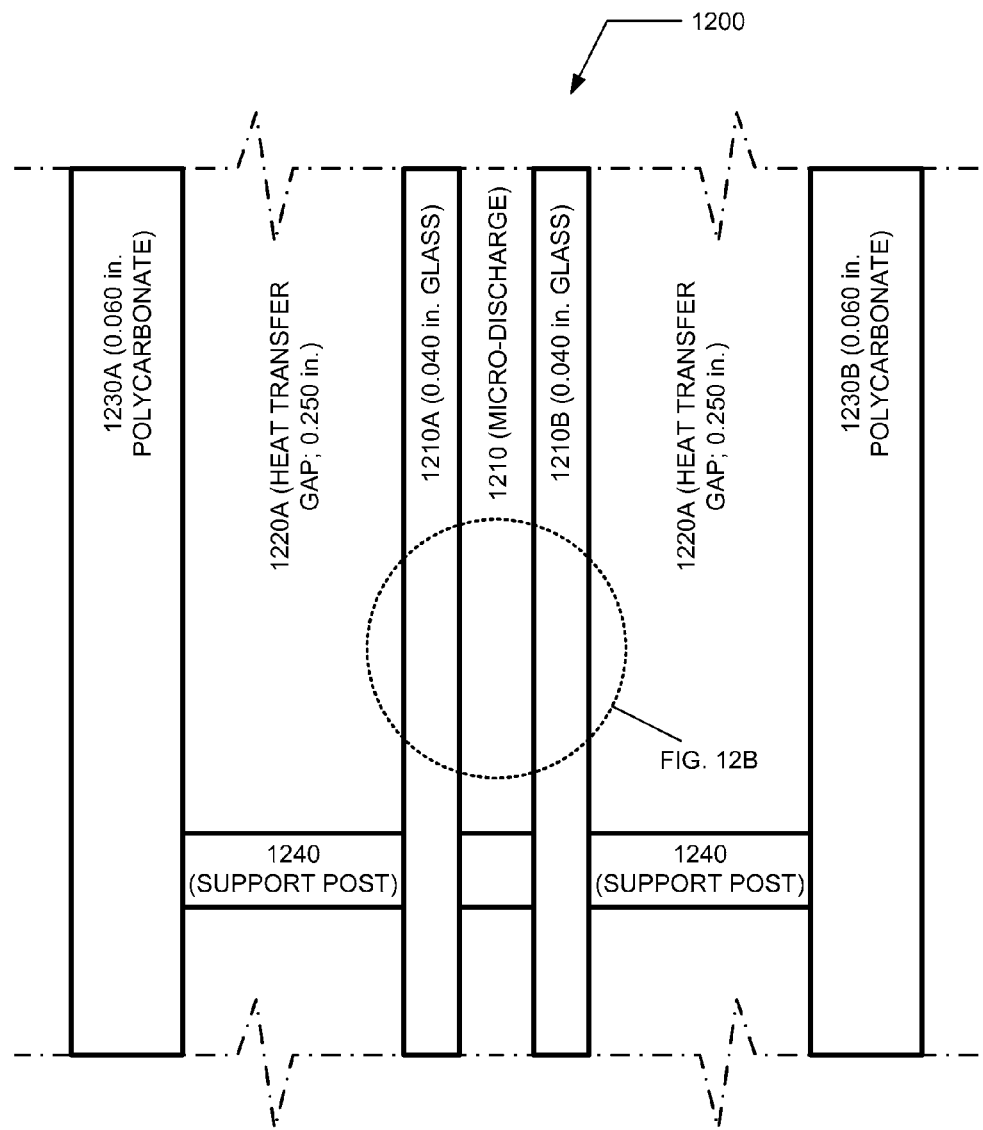
FIG. 12A provides a cross-sectional view of a portion of a light-emitting panel according to an embodiment.
Figure 12B:
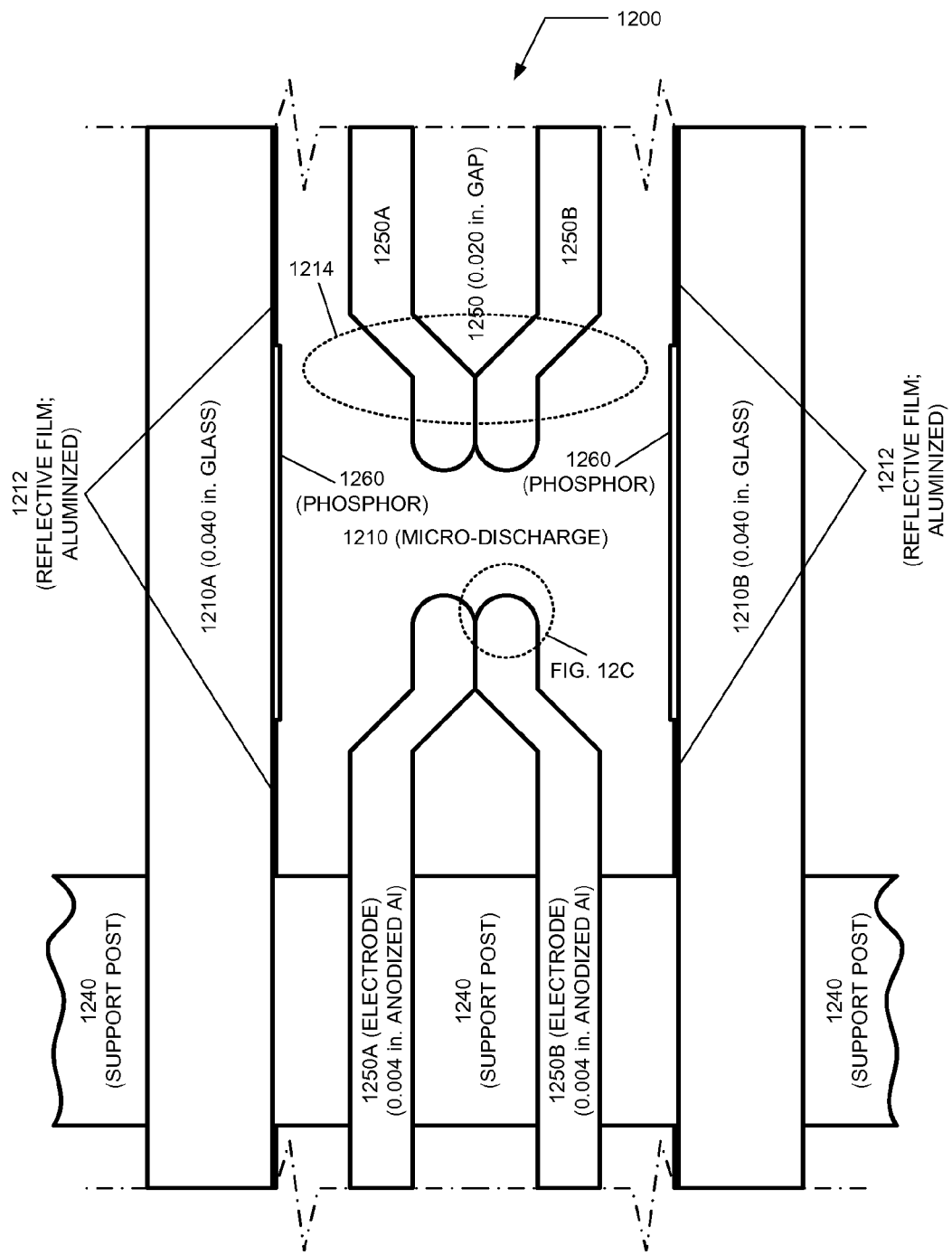
FIG. 12B provides an exploded view of a portion of the light-emitting panel depicted in FIG. 12A.
Figure 12C:
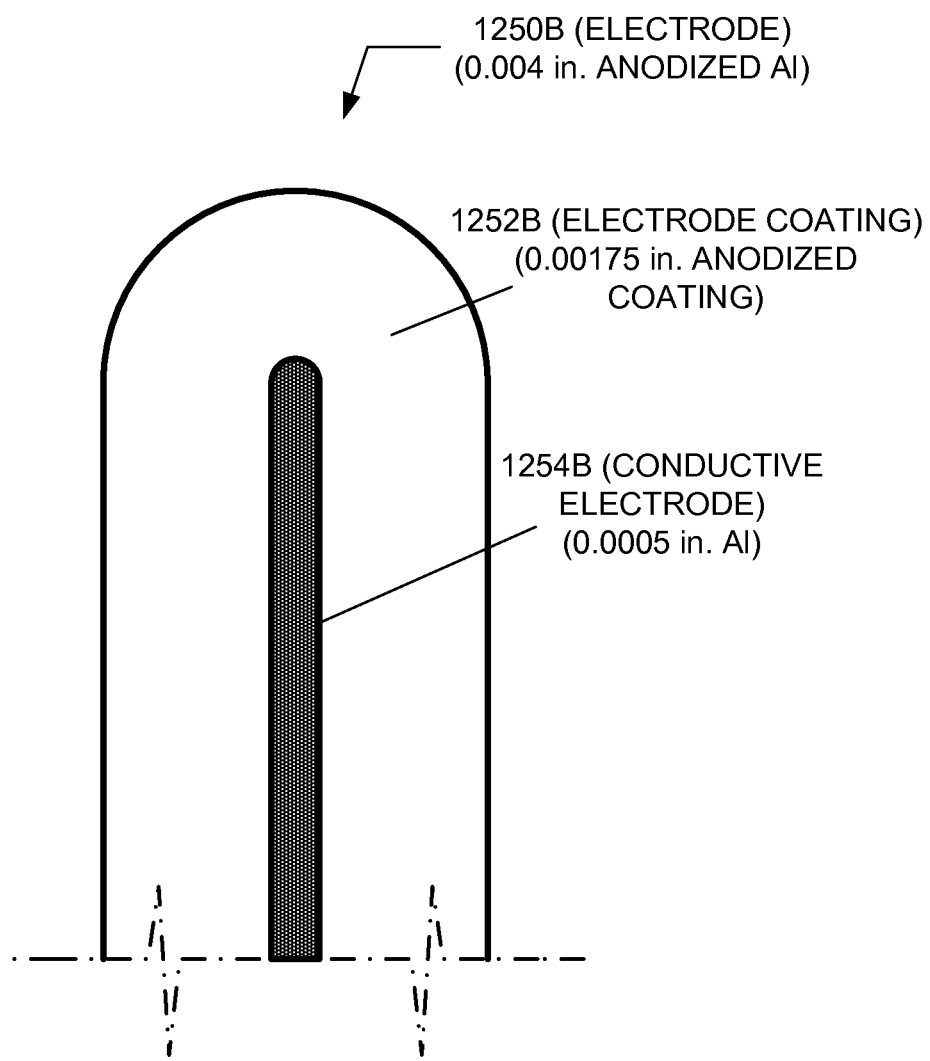
FIG. 12C provides an exploded view of a portion of the light-emitting panel depicted in FIG. 12B.

As shown in FIGS. 12A through 12C, a micro-discharge device 1200 may include a pair of electrodes (1250A, 1250B) (e.g., 0.004 inch (in.) anodized aluminum) separated by a gap 1250 (e.g., 0.020 in. gap). The pair of electrodes (1250A, 1250B) has a plurality of openings formed there through, wherein a micro-discharge 1210 is formed. Further, the pair of electrodes (1250A, 1250B) is suspended between two optically transparent plates (1210A, 1210B) (e.g., 0.040 in. thick glass that is optically transparent in the visible electromagnetic radiation spectrum). The two optically transparent plates (1210A, 1210B) are coated with a reflective film 1212 (e.g., a metal film, or an aluminum film) on an interior surface thereof, except for regions that are coated with a phosphor 1260. The regions coated with the phosphor 1260 align with the micro-discharge 1210 in the openings through the pair of electrodes (1250A, 1250B).

TABLE 1

| Microdischarge design with no dimples to reduce capacitance | |
|---|---|
| Dielectric constant aluminia | 9.8 |
| Dielectric constant free space | 8.85E−12 f/m |
| Dielectric thickness | 0.0035 inch |
| Dielectric thickness | 0.00889 cm |
| Dielectric thickness | 0.0000889 m |
| Capacitience | 9.76E−07 f/m^2 |
| Applied voltage | 300 volts |
| rise time | 1.00E−06 seconds |
| Inrush current | 2.93E+02 amps/m^2 |
| Density of discharges | 10000/m^2 |
| Discharge current | 0.00 amps |
| Discharge power | 0.30 watts |
| Discharge power density | 3000.00 watts/m^2 |
| Light conversion efficiency | 32.00% |
| Light output | 960.00 watts/m^2 |
| Discharge current | 10.00 amps/m^2 |
| Inrush/discharge current | 29.28 |
| Microdischarge design with dimples to reduce capacitance | |
| Dielectric constant aluminia | 9.8 |
| Dielectric constant free space | 8.85E−12 f/m |
| Dielectric thickness | 0.0035 inch |
| Dielectric thickness | 0.00889 cm |
| Dielectric thickness | 0.0000889 m |
| Air gap thickness | 0.02 inch |
| Air gap thickness | 0.0508 cm |
| Air gap thickness | 0.000508 m |
| Capacitience | 1.74E−08 f/m^2 |
| Applied voltage | 300 volts |
| rise time | 1.00E−06 seconds |
| Inrush current | 5.23E+00 amps/m^2 |
| Density of discharges | 10000/m^2 |
| Discharge current | 0.00 amps |
| Discharge power | 0.30 watts |
| Discharge power density | 3000.00 watts/m^2 |
| Light conversion efficiency | 32.00% |
| Light output | 960.00 watts/m^2 |
| Discharge current | 10.00 amps/m^2 |
| Inrush/discharge current | 0.52 |

An array of support post 1240 is utilized to affix and spatially locate each device component relative to one another between an optically transparent protective outer skin (1230A, 1230B) (e.g., 0.060 in. polycarbonate). Other materials, such as polyimide or polyester, may be used. A heat transfer gap (1220A, 1220B) (e.g., 0.250 in. thick) may be located between the protective outer skin (1230A, 1230B) and the pair of optically transparent plates (1210A, 1210B). The heat transfer gap (1220A, 1220B) may be configured to receive and circulate a heat transfer fluid that may be used to control a temperature of the light-emitting panel and/or the fluid medium within which the photosynthetic organisms are grown.

As shown in FIG. 12C, each of the pair of electrodes (1250A, 1250B) (e.g., 0.004 inch (in.) anodized aluminum) may include a conductive electrode 1254B (e.g., 0.0005 in. thick aluminum) having an electrode coating 1252B (e.g., 0.00175 in. thick surface anodization; anodized aluminum). During fabrication, the conductive electrodes (1254A, 1254B) may be paired together for forming the openings there through, then separated, anodized, re-aligned, and bonded to form the pair of electrodes (1250A, 1250B).

The micro-discharge may be operated in a rare gas or rare gas mixture, such as a Penning mixture (e.g., metastable of one gas may ionize the other, He:Ne being a classic example), that operates at a pressure of about 500 to 700 Torr.

Additional modifications to the micro-discharge for use in a light-emitting panel may include, but not be limited to, the following: (a) The pair of electrodes (1250A, 1250B) may be formed with a dimple 1214 at each opening for micro-discharge 1210 prior to anodization to minimize capacitance (see FIG. 12B and TABLE 1); (b) The optically transparent plate (1210A, 1210B) on the interior/discharge side may be provided with reflective film 1212; (c) The reflective film may be patterned to remove the reflective film 1212 at each location for micro-discharge 1210, wherein the phosphor 1260 is deposited; and (D) The array of support posts 1240 may continuously support the tension on the protective outer skin (1230A, 1230B) caused by pressure needed to flow the coolant fluid. The array of support posts 1240 may be glued in place. Short support posts may include dots of adhesive.

Light-Emitting Panel—Continued

The light-emitting panels may be arranged with photodetectors and filters to detect the light intensity, light timing, and functionality of opposing light-emitting panels, the cleanliness of various surfaces, and the clarity of the heat transfer fluid and/or the refractive index matching fluid.

Light-emitting panels may be fabricated by: (a) Using fiberglass pultrusions (extruded plastic part, injection formed plastic, molded fiberglass) parts to comprise a duct frame that supports a light-emitting panel pair (see FIGS. 10A, 10B, and 11.

(b) Fabricate a fiberglass pultrusion frame around smaller light-emitting panel sections to make a large light-emitting panel and allow for replacement of sections that fail, leak cooling fluid, leak media onto the circuit area or become to contaminated to remain clean in the growth environment.

(c) Fabricate the frames of light-emitting panels so that they are double sealed between different fluids and the volume between the seals is sensed for the fluid held off by the seals. This system detects seal failure before the fluids mix.

(d) Mount the light-emitting panel sections to the duct frame with a double o-ring seal with sensing between seal volume.

(e) A design to seal the duct frame to the light-emitting panel section, wherein the outer seal is inflatable and designed to fill the tolerance gap between the frame and the light-emitting panel section.

(f) Since the duct frame houses the individual light panel pairs. Add inflatable seals on the outside of and between frame duct elements to exclude growth media and minimize stagnant volumes of growth media and culture.

(g) Design duct with make-up media injection on the backside of duct frame to exclude growth media and minimize stagnant volume of growth media and culture.

(h) Design the light-emitting panels with a micro-discharge with these features: (i) One design of micro-discharge starts with paired thin aluminum sheet that are match drilled with small holes ~100 micrometers and then anodized with a special process that produces a interrupted columnar growth that has enhanced dielectric strength and durability. In this application we want to pulse the light and the pair of mated anodized plates have considerable capacitance that requires considerable inrush current to pulse quickly. In this application the density of discharge holes on the plate is relatively sparse thus enhancing the capacitance. In this design the sheets are dimpled (flat bottomed dimple) toward each other to keep them apart by a millimeter or so. (ii) The dimpling requires us to space the plates apart expect for the bottoms of the dimples where the plates (anodized) are touching. The space is generated by a dot of epoxy (low vapor pressure) and then rolling the part onto the existing structure. (iii) Pins in the sheets accurately align the plates during processing and are then removed, (iv) The plates are vacuum attached to plates for assembly and then the plates are removed. These plates allow for alignment of the holes and accurate setting of the gap above. (v) The outside of the microdischarge light source is a atmospheric barrier transparent surface. This surface is deposited with phosphor at each discharge location. Between the discharge locations the surface is metalized to be highly reflective. (vi) These screens are spaced off the dimpled plates by again dots of epoxy. Again the rolled assembly process. (vii) Second layer each side provides a fluid cooling passage. This passage gap is fixed by short post affixed by epoxy. (viii) The supports post and dots are aligned allowing for support of stress through the thin sheet and to the surfaces. With reasonable adhesion to the surfaces 1 mm diameter dots and post on a 2 cm grid interspersed with discharge locations on a 1 cm grid will reliability support a pressure or tension of 5-10 psi. (ix) The plates are of sufficient strength at 0.060 inch for most transparent plastic materials such as polycarbonate. (x) PCB edges are bonded to the aluminum plates with conductive epoxy and allow for electrical connection outside the controlled atmosphere of the microdischarge source.

(i) Design light panels using LEDs or LED lasers using the following: (i) Extrude a pultrusion element that is 2× inches wide and several feet long. This as described in figure attached. (ii) Make turn around in end pieces—the above makes a heat exchanger to cool the media and the waste LED heat. (iii) Make side parts as above. (iv) Laminate copper layer on fiberglass and pattern to make circuit. (v) Populate board with special pick and place machine.—(1) First option is to use bare die, (2) $2^{nd}$ option is to use surface mount chips, (3) Reflow or wave solder. (vi) Laminate with clear surface.—(1) $1^{st}$ options is to epoxy bond a clear laminate such as polycarbonate, (2) $2^{nd}$ option is to pot a layer of epoxy, (3) $3^{rd}$ is to heat acrylic and vacuum form onto circuit. (vii) Trim edges.

Multi-Sun Intensity

The intensity of the light is expected to be a multiple of the sun light spectra at the earth's surface integrated over the absorption spectra of chlorophyll A and B. More intense light produces more growth per unit area of the generating facility and leads directly to production efficiency of the plant. The inventors believe that light at 10-20 or more suns may be generated for photosynthetic organism growth. Additional light may eventually generate some photo inhibition that varies with species and sub species (natural or genetically modified).

Method

Figure 13:
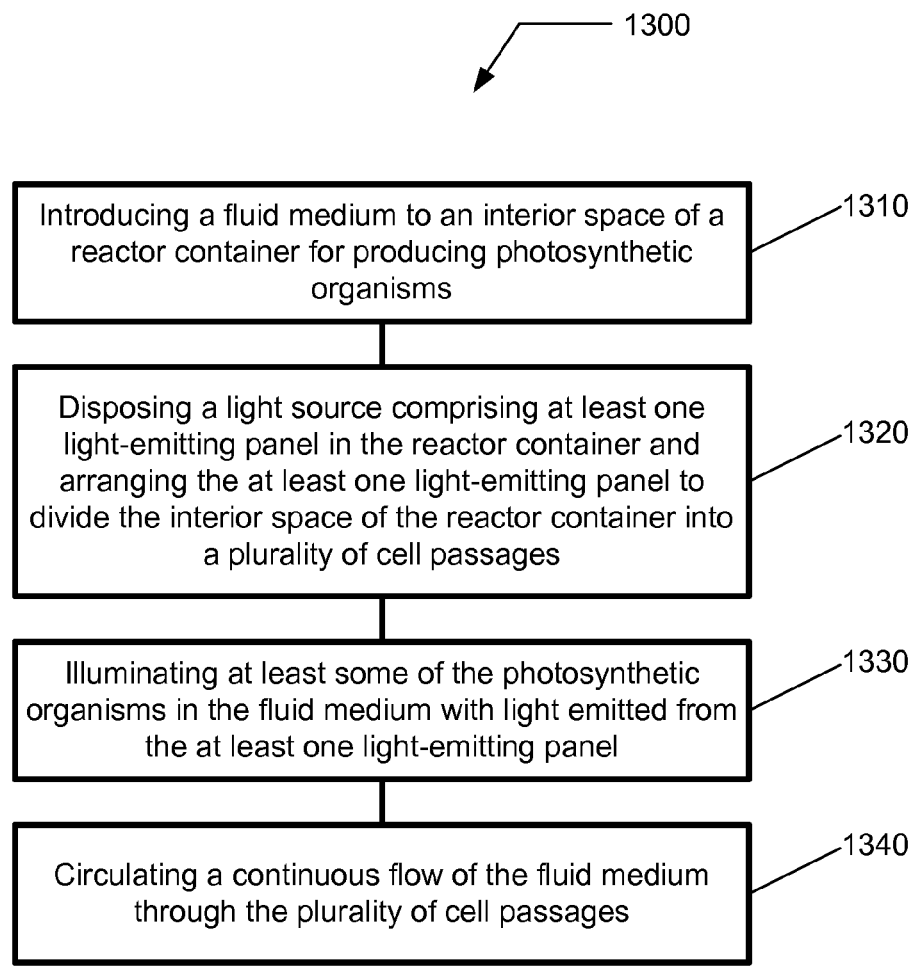
FIG. 13 provides a flow chart for performing a method of growing and harvesting photosynthetic organisms according to an embodiment.

FIG. 13 provides a method of method for growing and harvesting photosynthetic organisms according to an embodiment. The method includes a flow chart 1300 beginning in 1310 with introducing a fluid medium to an interior space of a reactor container for producing photosynthetic organisms.

In 1320, a light source comprising at least one light-emitting panel is disposed in the reactor container and arranged with at least one light-emitting panel to divide the interior space of the reactor container into a plurality of cell passages, wherein the at least one light-emitting panel has a first light-emitting surface and a second light-emitting surface on opposing sides of said light-emitting panel.

In 1330, at least some of the photosynthetic organisms in the fluid medium is illuminated with light emitted from said at least one light-emitting panel.

In 1340, a continuous flow of the fluid medium is circulated through the plurality of cell passages.

Figure 14:
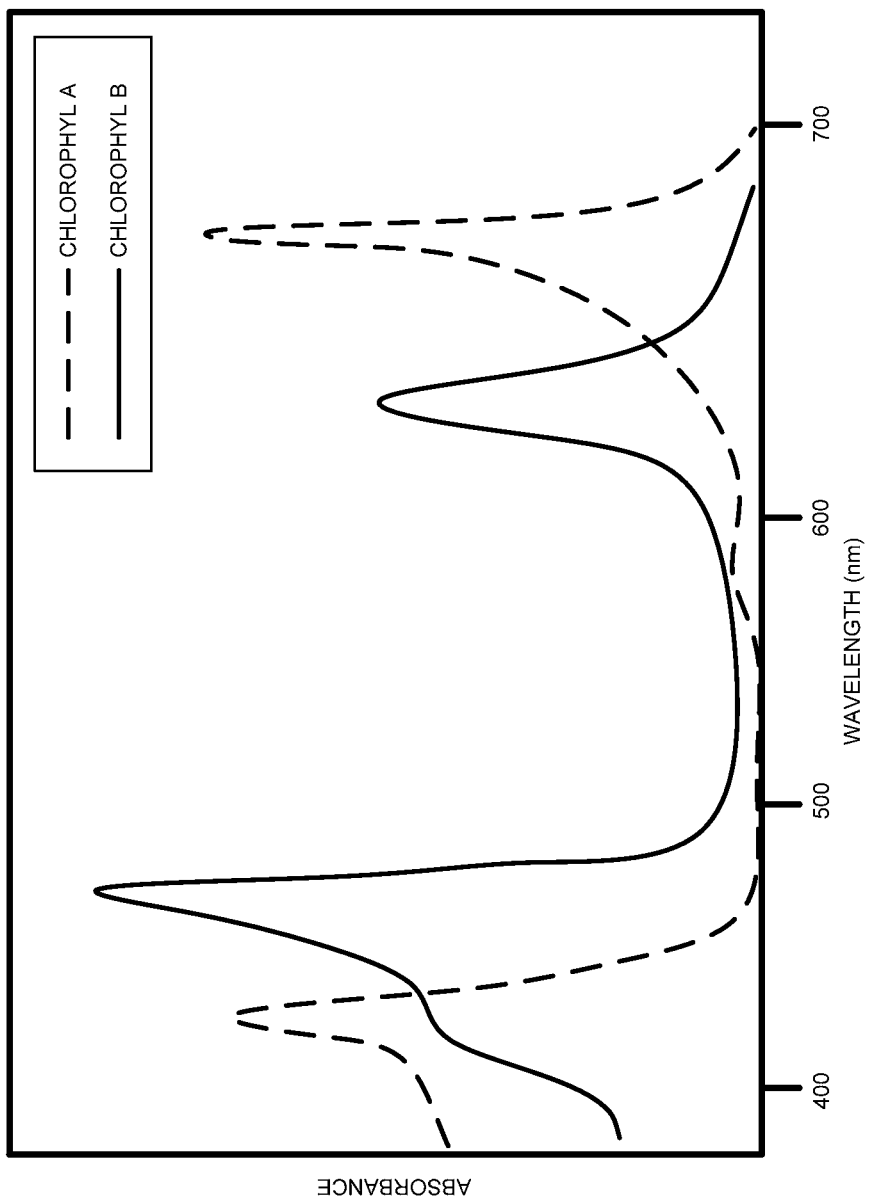
FIG. 14 provides exemplary absorption spectra for chlorophyll A and chlorophyll B.

FIG. 14 illustrates exemplary chlorophyll absorbance spectra.

Other Methods (a) The photo-bioreactor system may have an automatic harvest that is rate controlled to keep the density of photosynthetic organisms in the media substantially constant. This level of control may stabilize the growth environment and make the effect of process variations more readily discernable.

(b) Light source control, including control of pulse width, chlorophyll A and chlorophyll B light ratio, total light power, and various nutrient ratios by measuring response to oxygen generation may be used and confirmed by harvest rate. The control system may employ a differential algorithm to vary the process parameters continually to optimize growth rate. This system may use a multivariable self-learning that resolves the slope of each variable continuously.

(c) Light source control, including control of pulse width, chlorophyll A and chlorophyll B light ratio, total light power, and various nutrient ratios by measuring in-situ cell oil content measurement may be used and confirmed by lab measurement. The control system may employ a differential algorithm to vary the process parameters continually to optimize oil content. This system may use a multivariable self-learning that resolves the slope of each variable continuously.

(d) Light source control, including control of pulse width, chlorophyll A and chlorophyll B light ratio, total light power, and various nutrient ratios by measuring in-situ parameter measurement of a desired property or product may be used and confirmed by lab measurement. The control system may employ a differential algorithm to vary the process parameters continually to optimize the specific measurement content. This system may use a multivariable self-learning that resolves the slope of each variable continuously.

(e) The control system may "fingerprint" slopes to determine growth species health and help determine stability of the growth subspecies population.

(f) Algae is a very adaptable organism. Many methods may be used to stress the algae to induce blooming and/or enhance conversion of cell content to more oil, sub-fractions of oil such as omega-3 or omega-6, astaxanthin, or any number of desired products to be later separated from the growing material. Too mild an application of stress causes the algae to simply modify. Too stringent an application of stress causes the algae to shut down growth or, under extreme circumstance, perish. The control system may use various tuning/optimization methods to vary growth conditions and use the fingerprint slopes to manage the stress condition.

(g) Method to detect photo inhibition with slope fingerprints.

(h) Method to sort genetically modified species by microcell microscopy and FlowCam® system, commercially available from Fluid Imaging Technologies.

Cleaning (a) A soft brush and/or wiper blade system that moves in a slot between two light panels and optionally vacuums the material removed from the surface to harvest.

(b) A system of photo-detectors on the LED PCB boards that may detect the light emission from, for example, LEDs. The system has a software program that allows the flashing LED strings one string at a time to be turned on between the normal pulses. The pulses are detected on the opposing panel and the level of intensity is compared over time. This comparison determines if the strings are working correcting and when cleaning of the opposing panel pair is required.

(c) A double-sided camera system that can move under media across and along the depth of the panel under operation. The camera know where it is from information received from the PCB by either RF field, light emitting markers, sonic or other visual cues. This camera can expand to fill the flow gap. The faces of the camera are a flexible (silicone) material that expands on command to seal excluding media against the opposing faces and provide clear optical view of the PCB and its elements. This camera can allow magnified inspection of the LED board surface, access LED function and look for seal integrity under pressure and operation.

(d) A camera system that records the light intensity emitted from each panel (removed from the media) and record for each LED. This system is capable of less than 1% accuracy of intensity and spectra.

(e) A cleaning tank that allows for each panel once removed from the media racetrack to be treated in high-pressure spray, surface chemical treatment to kill any surface attached film and then neutralize and rinse the surface. This tank contains the spray and returns the effluent to remote storage tanks where it is cleaned and rejuvenated. This tank can be located in a central or several central locations of transported to the tank to minimize transport of relative fragile panels. Alternatively, the tank can be transported to the panel and operated close to the racetrack but not over the media to avoid costly contamination of the growing algae.

(f) Individual pairs can be removed for several minutes (enough time for and exchange with little impact on the growth process except for a part of a percent loss in growth rate.

(g) Placing auxiliary airlift membranes in the bottom of the tank to allow agitation and local lift during light panel pair exchange.

Harvesting

Disrupt using the following system: (a) Centrifuge down harvest ~25-100 g/liter (dry algae equivalent)—evaporate water to make salt;

(b) Rinse in fresh water;

(c) Centrifuge down rinsed flow to ~25-100 g/liter (dry Algae equivalent)—evaporate water to make salt;

(d) Pressurize to 750 psi;

(e) Inject $CO_2$ as a liquid;

(f) Pressurize using high pressure pump to a pressure of ~30,000 psi;

(g) Hold at pressure for a time to allow the $CO_2$ to diffuse into the cells;

(h) Expand onto a turbine wheel that drives a generator and recovers the energy;

(i) Recapture the $CO_2$ clean and reuse; and (j) Centrifuge separate: (i) Oil stream further processed when using normal processing steps to produce refined, bleached, and deodorized (RBD) oil or less processed if feasible. (ii) Cell residual processed by: (1) Rinse, centrifuge, and extract low concentration products from the cell material. (2) Transport cell material to ethanol production. (3) After ethanol processing, transport residual of ethanol production (protein and waste material) to animal feed. (iii) Transport the water residual to a plant to evaporate water to recover the salt.

Integrate as described in the integrated flow system of FIG. 1:

(a) The $CO_2$ loop uses: (i) $CO_2$ from ethanol production, (ii) $CO_2$ from digester, (iii) $CO_2$ from turbine generators, and (iv) $CO_2$ from air extraction to inject into the growth media to promote algae growth.

(b) The methane loop uses: (i) Methane from digester, (ii) Natural gas from pipeline to generate power that is used to shift the power needs from the grid to off-peak time.

(c) The low grade heat loop collects: (i) Heat from the turbine generator exhaust, (ii) Heat from the ethanol distillery, and uses the collected heat to evaporate waste water and heat the digester, as well as provide space heat.

(d) Add method to treat animal waste to reclaim phosphorus and nitrogen to use as fertilizer for algae.

Other Embodiments (1) Folded air, nitrogen and/or CO2 lift and mix with each pair of light plates allows for maximum surface area in smallest floor space.

(2) Nutrient injection as frequently as each light plate.

(3) Analysis of water, algae density after several light plates to reduce the cost of analysis equipment.

(4) Light panels arranged in a racetrack configuration, such as a serpentine racetrack, with the length of racetrack designed to: (a) Harvest every lap, (b) Analyze every lap, (c) Perform a phase of growth every lap.

(5) Light panels and airflow controlled independently to stress algae to enhance products—lipids, protein or carbohydrates.

(6) Light panel controlled by opposite panel to provide optimum intensity and thus adapt to a range of algae density (g/liter) allowing: (a) Fixed spacing of harvest points without function non optimum growth conditions, (b) Wide range operation for enhancing stress conditions to enhance specific growth products results.

(7) Light panels that are synchronized to pulse the light flux together in a single unit of algae.

(8) A similar bridge that supports the cleaning system.

(9) A similar bridge that supports the inspection camera.

(10) Cover for racetrack of mostly opaque material fiberglass that collects gas evolved from the media and vents it to the roof. The cover protects personnel from the high light intensity in the reactor container. The cover also protects the reactor plant from excessive oxygen levels (produced by the algae) that may become a fire hazard. Flexible connection to the vent pipe allows the cover to be removed and stored in the overhead during maintenance operations. Larger covers are sectioned to allow easy removal. Rubber seals and roof mounted vent blower that maintain negative pressure at seal points insure reliable exit of gases to roof.

(11) A drivable (self-propelled electric on retractable wheels around the plant) bridge that spans the bank and allows operators to access the bath. This unit can move the length of the racetrack by tracks build on the concrete racetrack walls. Can be set through indicators (bar codes) on individual light panel pairs or specific positions. Data system allows operation to see history of individual light panels to enhance speed of making maintenance decisions.

(12) Light panels designed as follows: (a) Mineral oil (or other fluid) cooling of the LED and circuitry power and media adsorbed power (aeration lift power and light adsorbed) that provides some index matching between the polycarbonate media barrier and the LED or plasma panel, (b) Point sources of light that are intense and pulsed using distributed pulse circuitry, (c) Highly reflective surfaces between sources of light to reflect unused light power back into the media, (d) Panel mounting features allowing for very large panels up to 48 ft wide by 100 ft. long. Longer panels allow for a lower tank wall count but deeper tanks require thicker walls and longer panels require taller building. Deeper tanks require high aeration/lift pressure but lower flow rates. Wider panels require more space for turn around area and make for a more fragile structure or a thicker panel that cost more.

(13) Use of more specific light sources with special capability as follows: (a) Blue LED driven phosphors with better match to adsorption spectra of chlorophyll a and b on the red end and/or blue end. (b) Discrete driving of A and B chlorophyll spectra as different times and intensities. (c) Micro-discharge light sources to drive multiple bright spot sources. Bright spots sources may consist of multiple of micro-discharge channels. (d) The concept of driving the short pulsed at many times the equivalent solar spectra in the red and or blue chlorophyll adsorption spectra.

(14) Coupling the concepts of concentrated solar and algae cultivation.

(15) Coupling concepts in attached flow chart and the feedback of animal waste for fertilizer for the algae. Other integration with sewage, water treatment systems and agriculture system.

(16) Coupling the concepts for integrated energy management: (a) Methane (from fermentation and generation from animal waste) stored for off solar hours power generation, (b) Integration of heat sources to dry some meal for shipment, (c) Integration of cooling system to a central cooling tower.

(17) Light panels that are comprised of polyester, polyimide, or polycarbonate, such as Mylar™, Kapton™, Lexan™, and/or plastic layers and flexi-circuits as follows: (a) A flow circuit made by welding or bonding two membranes in a pattern to generate a passage for fluid flow to cool the circuit and the bath. (b) A second flow circuit made by welding or bonding two membranes in a pattern to generate a passage for fluid that can expand the outer surfaces of the light panel. When activated, these surfaces move the growth media and algae in such a way that it is pumped at a speed ~1 ft/sec or a speed at which the organism is kept in suspension. (c) A flexi circuit upon which the driving devices and LED are attached. (d) A reflective surface with holes for the LED to emit light for purposes of reflecting the light not adsorbed by the algae n the media in the first pass. (e) A sealing membrane to protect the circuit and reflective surface from the corrosive action of the media. (f) Light panels above but without the peristaltic function. (g) Light panels above but with some aeration and $CO_2$ injections as before. Therefore, pumping is a combination of airlift and peristaltic effect. (h) Light panels above with various diagnostic devices, photo-detectors and/or sensors attached. (i) Method to make above using reel to real techniques. (j) Methods to remove the above from the bath using reel techniques. (k) Methods to clean the above using reel-to-reel techniques. (l) Methods to move the light panels on a large loop through the media continuously and clean continuously.

Although only certain embodiments of this invention have been described in detail above, those skilled in the art will readily appreciate that many modifications are possible in the embodiments without materially departing from the novel teachings and advantages of this invention. Accordingly, all such modifications are intended to be included within the scope of this invention.

The invention claimed is:

1. A photo-bioreactor system for growing and harvesting photosynthetic organisms, comprising:

a reactor container having an interior space partitioned into a plurality of independently controlled reactor cells configured to receive and hold a fluid medium for growing photosynthetic organisms, wherein said plurality of cells are stepped downward along a slope from a first elevation to a second elevation, lower than said first elevation, to allow gravity to assist a continuous flow of fluid medium downwardly from reactor cell to adjacent reactor cell;

a light source coupled to each of said plurality of reactor cells in said reactor container and configured to illuminate at least some of said photosynthetic organisms in said fluid medium, said light source comprising a controller for independently controlling a plurality of light-emitting panels extending vertically into said reactor container and dividing said interior space of said reactor container into a plurality of vertically oriented cell passages, wherein each of said plurality of light-emitting panels have a first light-emitting surface and a second light-emitting surface on opposing sides of said light-emitting panel; and a fluid circulation system coupled to said reactor container and configured to force said continuous flow of said fluid medium through said plurality of cell passages by pumping said continuous flow of said fluid medium from a reactor cell at said second elevation to a reactor cell at said first elevation, wherein at least one reactor cell includes a downward flowing passage and an upward flowing passage, and wherein at least one reactor cell includes an outlet edge of a vertical outlet wall, over which said fluid medium flows out of the at least one reactor cell, that is lower than an inlet edge of a vertical inlet wall, over which said fluid medium flows into the at least one reactor cell.

2. The photo-bioreactor of claim 1, wherein said continuous flow follows a serpentine flow path that includes a flow path segment extending along said first light-emitting surface, a flow path segment passing around a distal end of said at least one light-emitting panel, and a flow path segment extending along said second light-emitting surface.

3. The photo-bioreactor of claim 1, wherein said continuous flow follows a parallel flow path that includes a first flow path segment extending along said first light-emitting surface, and a second flow path segment extending along said second light-emitting surface, and wherein said first flow path segment and said second flow path segment are parallel and aligned in the same direction.

4. The photo-bioreactor of claim 1, wherein said plurality of light-emitting panels are spaced apart at intervals along a first direction within said interior space of said reactor container, wherein said intervals define said plurality of cell passages extending between light-emitting surfaces of adjacent light-emitting panels.

5. The photo-bioreactor of claim 1, wherein said fluid circulation system injects a fluid into said fluid medium within at least one of said plurality of cell passages to generate a buoyancy-driven channel flow through said at least one cell passage.

6. The photo-bioreactor of claim 1, wherein said fluid circulation system injects a fluid into said fluid medium within said reactor container, said fluid containing one or more nutrients for supporting the growth of said photosynthetic organisms, air, nitrogen, or carbon dioxide, or any combination of two or more thereof.

7. The photo-bioreactor of claim 1, wherein at least one of said plurality of cell passages comprises a uniform cell passage having a cross-sectional area that is substantially constant along at least a portion of said serpentine flow path.

8. The photo-bioreactor of claim 1, wherein at least one of said plurality of cell passages comprises a convergent cell passage having a cross-sectional area that decreases along a direction of said continuous flow.

9. The photo-bioreactor of claim 1, further comprising:
photosynthetic organism harvester coupled to said reactor container and configured to extract at least some of said photosynthetic organisms grown in said reactor container.

10. The photo-bioreactor of claim 9, wherein said light source comprises a first array of light-emitting panels spaced apart at first intervals along a first direction within a first interior space of said reactor container, wherein said first intervals define at least one cell passage extending between light-emitting surfaces of adjacent light-emitting panels in said first array, wherein said light source further comprises a second array of light-emitting panels spaced apart at second intervals along a second direction within a second interior space of said reactor container, wherein said second intervals define at least one cell passage extending between light-emitting surfaces of adjacent light-emitting panels in said second array, wherein said continuous flow includes a first serpentine flow path extending through said first array of light-emitting panels in said first direction and a second serpentine flow path, fluidically coupled to a distal end of said first serpentine flow path, extending through said second array of light-emitting panels in said second direction, opposite said first direction, and wherein said first serpentine flow path and said second serpentine flow path form a lap in said reactor container.

11. The photo-bioreactor of claim 10, wherein said photosynthetic organism harvester extracts said photosynthetic organisms at each lap within said reactor container, or several placed per lap.

12. The photo-bioreactor of claim 1, wherein said light source is configured to illuminate at least some of said photosynthetic organisms with light comprising one or more peak light emission corresponding to an absorption spectrum for chlorophyll A and/or chlorophyll.

13. The photo-bioreactor of claim 1, wherein said light source is configured to illuminate at least some of said photosynthetic organisms with light comprising one or more peak light emission including an emission wavelength in the range from about 440 nanometers (nm) to about 660 nm.

14. The photo-bioreactor of claim 1, wherein said light source comprises one or more light-emitting diodes (LEDs), or one or more light-emitting micro-cavity plasma discharges, or a combination thereof.

15. The photo-bioreactor of claim 1, wherein said light source comprises phosphor emission, and wherein said phosphor comprises an oxide, a nitride, an oxynitride, a phosphide, a sulfide, a selenide, a halide, or a silicate of zinc, cadmium, manganese, aluminum, silicon, or rare earth metal.

16. The photo-bioreactor of claim 1, further comprising:
a nutrient supply system coupled to said reactor container and configured to introduce one or more nutrients for supporting the growth of said photosynthetic organisms, wherein said one or more nutrients are suitably treated, filtered, aerated, or supplemented with additional nutrients, or any combination thereof, or a nutrient recovery system coupled to said reactor container, and configured to recover at least some of said one or more nutrients and re-introduce the recovered nutrients to said reactor container, or a monitoring system coupled to said reactor container, and configured to sense one or more processing parameters, said one or more processing parameters including a concentration of one or more nutrients, a concentration of said photosynthetic organism, a fluid level for said fluid medium, a pH for said fluid medium, a flow rate for said continuous flow, or a lighting property of said light source, or any combination of two or more thereof, or a control system coupled to said photo-bioreactor, and configured to control one or more processing parameters for optimizing production of said photosynthetic organism, or a cleaning system coupled to said photo-bioreactor, and configured to facilitate cleaning of one or more surfaces on said at least one light-emitting panel and/or said reactor container, or a vent system coupled to said photo-bioreactor, and configured to exhaust excess gas from said reactor container, or a heat exchanger coupled to said reactor container, and configured to adjust and/or control a temperature of said fluid medium, or a maintenance bridge configured to span said reactor container and allow inspection, reactor component installation, reactor component extraction for remote maintenance, and/or cleaning of said reactor container or any reactor component therein, or any combination of two or more thereof.

17. The photo-bioreactor of claim 1, wherein said fluid circulation system includes a low shear pump, or an Archimede's screw pump.

18. The photo-bioreactor of claim 1, further comprising:
an actuator coupled to said reactor container and configured to adjust an elevation of at least one of said plurality of reactor cells, or
an actuator coupled to said reactor container and configured to adjust the slope of said plurality of reactor cells.

19. The photo-bioreactor of claim 1, wherein said continuous flow of fluid medium moves along a serpentine flow path from reactor cell to adjacent reactor cell.

20. The photo-bioreactor of claim 1, further comprising: a light source controller coupled to said light source and configured to pulse light emission from said light source into said fluid medium.

* * * * *